United States Patent
Ofek et al.

(10) Patent No.: US 7,435,716 B2
(45) Date of Patent: Oct. 14, 2008

(54) COMPOUNDS PHARMACEUTICAL COMPOSITIONS AND METHODS FOR TREATMENT OF BACTEREMIA AND/OR SEPTICEMIA

(75) Inventors: Itzhak Ofek, Givataim (IL); Matityahu Fridkin, Rehovot (IL); Haim Tsubery, Ramat Gan (IL)

(73) Assignees: Ramot At Tel Aviv University Ltd., Tel-Aviv (IL); Yeda Research and Development Co. Ltd., Rechovot (IL)

( * ) Notice: Subject to any disclaimer, the term of this patent is extended or adjusted under 35 U.S.C. 154(b) by 392 days.

(21) Appl. No.: 10/451,795

(22) PCT Filed: Jan. 16, 2002

(86) PCT No.: PCT/IL02/00038

§ 371 (c)(1),
(2), (4) Date: Jul. 15, 2003

(87) PCT Pub. No.: WO02/055543

PCT Pub. Date: Jul. 18, 2002

(65) Prior Publication Data
US 2004/0082505 A1  Apr. 29, 2004

Related U.S. Application Data
(60) Provisional application No. 60/261,212, filed on Jan. 16, 2001.

(51) Int. Cl.
*A61K 38/02* (2006.01)
*A61K 38/08* (2006.01)
*A61K 38/10* (2006.01)
*A61K 38/12* (2006.01)
*C07K 2/00* (2006.01)
*C07K 7/00* (2006.01)

(52) U.S. Cl. .............................. 514/2; 514/11; 514/13; 514/14; 514/15; 530/300; 530/319; 530/326; 530/327; 530/345

(58) Field of Classification Search ..................... None
See application file for complete search history.

(56) References Cited

U.S. PATENT DOCUMENTS

| | | | | |
|---|---|---|---|---|
| 4,427,660 A * | 1/1984 | Schiffman et al. | ............ | 514/18 |
| 5,484,885 A * | 1/1996 | Pereira et al. | ............... | 530/326 |
| 5,780,429 A * | 7/1998 | Wainwright | ................ | 514/12 |
| 5,925,659 A * | 7/1999 | Patchett et al. | ............. | 514/374 |
| 6,733,997 B1 * | 5/2004 | Ding et al. | ................ | 435/69.8 |
| 6,861,053 B1 * | 3/2005 | Lin et al. | .................. | 424/93.1 |
| 2001/0026810 A1 * | 10/2001 | McGhee et al. | ............. | 424/486 |
| 2002/0049205 A1 * | 4/2002 | Li et al. | .................... | 514/236.8 |

OTHER PUBLICATIONS

Bycroft et al. Antibacterial and Immunostimulatory Properties of Chemotactic . . . Antimicrobial Agents And Chemotherapy. Sep. 1989, vol. 33, No. 9, pp. 1516-1521.*

(Continued)

*Primary Examiner*—Jeffrey E Russel

(57) ABSTRACT

Novel conjugates of bacterial outer membrane binding peptides, preferably having bacterial sensitization activity, and immune cells chemotactic peptides, and pharmaceutical compositions containing same useful in the treatment of bacteremia and/or septicemia following infection by gram negative bacteria administered alone or in combination with conventional antibiotics.

102 Claims, 1 Drawing Sheet

OTHER PUBLICATIONS

Appelmelk et al. Analytical Biochemistry. Dec. 1992, vol. 207, No. 2, pp. 311-316.*
Amoscato et al. Peptides. May-Jun. 1984. vol. 5, No. 4, pp. 489-494.*
Tsubery et al. Biochemistry. Oct. 2000, vol. 39, No. 39, pp. 11837-11844.*
Tsubery et al. Journal Of Medicinal Chemistry. Aug. 2000, vol. 43, No. 16, pp. 3085-3092.*
Tsubery et al. Advances In Experimental Medicine And Biology. 2000, vol. 479, pp. 219-222.*
Ofek et al. Antimicrobial Agents And Chemotherapy. Feb. 1994, vol. 38, No. 2, pp. 374-377.*
Tsubery et al. Peptides. Oct. 2001, vol. 22, No. 10, pp. 1675-1681.*
Appelmelk et al. "Polymyxin B-Horseradish Peroxidase Conjugates as Tools in Endotoxin Research". Analytical Biochemistry, 207(2): 311-316, 1992.
Amoscato et al. "Synthesis and Biological Activity of [L-3,4-Dehydroproline3]-Tuftsin." Peptides, 5(3): 489-494, 1984.
Tsubery et al. "The Functional Association of Polymyxin B With Bacterial Lipopolysaccharide Is Stereospecific: Studies on Polymyxin B Nonapeptide", Biochemistry, 39(39): 11837-11844, 2000.
Tsubery et al. "Structure-Function Studies of Polymyxin B Nonapeptide: Implications to Sensitization of Gram-Negative Bacteria", Journal of Medicinal Chemistry, 43(16): 3085-3092, 2000.
Tsubery et al. "Structure Activity Relationship Study of Polymyxin B Nonapeptide", Advances in Experimental Medicine and Biology, 479: 219-222, 2000.
Tsubery et al. "N-Terminal Modifications of Polymyxin B Nonapeptide and Their Effect on Antibacterial Activity", Peptides, 22(10): 1675-1681, 2001.
Athamna et al. "Enzyme-Linked Immunosorbent Assay for Quantitation of Attachment and Ingestion Stages of Bacterial Phagocytosis", Journal of Clinical Microbiology, 26(1): 62-66, 1988.
Athamna et al. "Lectinophagocytosis of Encapsulated Klebsiella Pneumoniae Mediated by Surface Lectins of Guinea Pig Alveolar Macrophages and Human Monocyte-Derived Macrophages", Infection and Immunity, 59(5): 1673-1682, 1991.
Becker "Some Interrelations of Neutrophil Chemotaxis, Lysosomal Enzyme Secretion, and Phagocytosis as Revealed by Synthetic Peptides", American Journal of Pathology, 85: 385-394, 1976.
Bryan "Mechanisms of Resistance to Antibacterial Agents", In: 'Bacterial Resistance and Susceptibility to Chemotherapeutic Agents', Cambridge University Press, Chap.3: 69-80, 1982.
Chihara et al. "Chemical Synthesis, Isolation and Characterization of α-N-Fattyacyl Colistin Nonapeptide With Special Reference to the Correlation Between Antimicrobial Activity and Carbon Number of Fattyacyl Moiety", Agricultural Biology and Chemistry, 38(3): 521-529, 1974.
Chihara et al. "Enzymatic Degradation of Colistin Isolation and Identification of α,γ-Diaminobutyric Acid and Colistin Nonapeptide", Agricultural Biology and Chemistry, 37(11): 2455-2463, 1973.
Chin et al. "Resistance to Antibiotics", Science, 264: 359-393, 1994.
Danner et al. "Purification, Toxicity, and Antiendotoxin Activity of Polymyxin B Nonapeptide", Anitmicrobial Agents and Chemotherapy, 33(9): 1428-1434, 1989.
Duwe et al. "In Vitro Cytotoxicity and Antibiotic Activity of Polymyxin B Nonapeptide", Antimicrobial Agents and Chemotherapy, 30(2): 340-341, 1986.
Freer et al. "Further Studies on the Structural Requirements for Synthetic Peptide Chemoattractants", Biochemistry, 19: 2404-2410, 1980.
Freer et al. "Formyl Peptide Chemoattractants: Model of the Receptor on Rabbit Neutrophils", Biochemistry, 21: 257-263, 1982.
Kitamura-Matsunaga et al. "Enzymic Preparation of Colistin Fragments and Their Biological Activity", Peptide Chemistry, 22: 333-338, 1984. Abstract.
Lam et al. "Membrane-Disorganizing Property of Polymyxin B Nonapeptide", Journal of Antimicrobial Chemotherapy, 18: 9-15, 1986.
Metcalf et al. "Functions Related to Microbicidal Activity", Laboratory Manual of Neutrophil Function, Chap.5: 87-90, 1986.
Morrison et al. "Binding of Polymyxin B to the Lipid A Portion of Bacterial Lipopolysaccharides", Immunochemistry, 13: 813-818, 1976.
Niedel et al. "Formyl Peptide Chemotactic Receptors of Leukocytes and Macrophages", Current Topics in Cellular Regulation, 17: 137-169, 1980.
Ofek et al. "Antibacterial Synergism of Polymyxin B Nonapeptide and Hydrophobic Antibiotics in Experimental Gram-Negative Infections in Mice", Antimicrobial Agents and Chemotherapy, 38(2): 374-377, 1994.
Ofek et al. "Nonopsonic Phagocytosis of Microorganisms", Annual Reviews in Microbiology, 49: 239-276, 1995.
Rustici et al. "Molecular Mapping and Detoxification of the Lipid A Binding Site by Synthetic Peptides", Science, 259: 361-365, 1993.
Schiffmann et al. "N-Formylmethionyl Peptides as Chemoattractants for Leucocytes", Proc. Natl. Acad. Sci. USA, 72(3): 1059-1062, 1975.
Søgaard "The Pharmacodynamics of Polymyxin Antibiotics With special Reference to Drug Restistance Liability", J. Vet. Pharmacol. Therapy, 5: 219-231, 1982.
Vaara "Agents That Increse the Permeability of the Outer Membrane", Microbiological Reviews, 56(3): 395-411, 1992.
Vaara et al. "Binding of Polymyxin B Nonapeptide to Gram-Negative Bacteria", Antimicrobial Agents and Chemotherapy, 27(4): 548-554, 1985.
Vaara et al. "Polycations Sensitize Enteric Bacteria to Antibiotics", Antimicrobial Agents and Chemotherapy, 24(1): 107-113, 1983.
Voitenko et al. "Relationship Between Structure and Histamine Releasing Action of Polymyxin B and Its Analogues", Agents and Actions, 30(½): 153-156, 1990.
Young "Gram-Negative Sepsis", In: 'Principles and Practice of Infectious Diseases', Wiley & Sons, Section E, Chap.54: 452-475, 1985.
Chihara et al. "Chemical Synthesis, Isolation and Characterization of ?-N-Fattyacyl Colistin Nonapeptide With Special Reference to the Correlation Between Antimicrobial Activity and Carbon Number of Fattyacyl Moiety", Agricultural Biology and Chemistry, 38(3): 521-529, 1974.
Chihara et al. "Enzymatic Degradation of Colistin Isolation and Identification of ?,?-Diaminobutyric Acid and Colistin Nonapeptide", Agricultural Biology and Chemistry, 37(11): 2455-2463, 1973.
EP/Summons to Attend Oral Proceedings of EP Application 02715695.6 dated Feb. 8, 2008.
EP Brief Communication of Apr. 22, 2008 on Oral Proceedings of May 7, 2008.
Obrist et al. "Conjugation Behaviour of Different Monoclonal Antibodies to F-Methionyl-Leucyl-Phenylalanine", International Journal of Immunopharmacology, 8(6): 629-632, 1986.
Rose et al. "Targeting Lipopolysaccharides by the Nontoxic Polymyxin B Nonapeptide Sensitizes Resistant *Escherichia coli* to the Bactericidal Effect of Human Neutrophils", The Journal of Infectious Diseases, 182: 191-199, 2000.
Tsubery et al. "Neopeptide Antibiotics That Function as Opsonins and Membrane-Permeabilizing Agents for Gram-Negative Bacteria", Antimicrobial Agents and Chemotherapy, 49(8): 3122-3128, 2005.

* cited by examiner

COMPOUNDS PHARMACEUTICAL COMPOSITIONS AND METHODS FOR TREATMENT OF BACTEREMIA AND/OR SEPTICEMIA

RELATED PATENT APPLICATION

This application is a National Phase Application of PCT/IL02/00038 International Filing Date 16 Jan. 2002, which claims priority from U.S. Provisional Patent Application No. 60/261,212 filed 16 Jan. 2001.

FIELD AND BACKGROUND OF THE INVENTION

The present invention relates to compounds, pharmaceutical compositions and methods for the treatment of bacteremia and septicemia and, more particularly, to novel conjugates of bacterial outer membrane binding peptides, preferably having bacterial sensitization activity, and immune cells chemotactic peptides, and pharmaceutical compositions containing same useful in the treatment of bacteremia and/or septicemia following infection by gram negative bacteria, administered alone or in combination with conventional antibiotics.

Blood infection caused by gram-negative bacteria is one of the major challenges facing modern medicine, despite treatment availability with conventional antibiotics (Young, 1985). Mortality rates in the range of 25-40% for gram-negative septicemia have been reported in some medical centers. Antibiotic treatment is often administered at late stages of the disease, usually when symptoms appear. The time required by the antibiotic to kill the pathogen is often too long, thus failing to prevent irreversible tissue damage. Moreover, in many cases the antibiotic is given before performing any sensitivity tests. The emergence of strains resistant to the conventional antibiotics and lack of rapid diagnosis and antibiotic sensitivity pattern of the infecting bacteria are probably among the major causes of the inadequate conventional therapy and high mortality (Cassel, 1995; Chin & Marks, 1994).

Polymyxins:

Polymyxins are basic cyclic peptides having a lipid moiety and antibiotic activity, naturally produced by various strains of *Bacillus polymyxa*. Of the many isolated and characterized polymyxins, only polymyxin B and E (the latter is also known as colistin) were in actual therapeutic use (Lambert and O'grade 1992). Polymyxin B is a polycationic amphipathic decapeptide, a potent bactericidal agent against most gram-negative bacteria. Emergence of resistant strains to polymyxin B has been reported to be rare (Soogard, 1982). Polymyxin B binds to the outer membrane of the bacteria (Morrison and Jacobs, 1976), and inserts its lipid moiety into the membrane to completely disorganize it (Bryan, 1982). The clinical use of polymyxins has been restricted, however, because polymyxins are highly toxic to animal cells.

Polymyxin Derived Peptides:

The removal, by deacylation, of the fatty-acid side chain from polymyxins, e.g., polymyxin B and E, significantly reduces the toxicity of the parent molecules (Vaara 1992). The deacylated product of polymyxin B, which is known as polymyxin B-derived peptide (PMBP) and alternatively as polymyxin B nonapeptide (PMBN), lacks bactericidal activity but retains its ability to bind specifically to the lipopolysaccharide (LPS) of the outer leaflet of the bacterial membrane and renders the gram-negative bacteria susceptible to several antibiotics by permeabilizing their outer membrane. The latter antimicrobial activity of PMBP is referred to in the art as sensitizing activity.

Because the parent polymyxin B molecule and its derivative PMBP bind to the same receptor on the bacterial surface, probably via the cyclic heptapeptide portion, the emergence of strains resistant to the sensitizing activity of PMBP is rare, as is the case for the bactericidal activity of the parent polymyxin molecule (Chihara et al., 1973; Vaara and Vaara, 1983; Duwe et al., 1986, Ofek et al., 1994).

Formyl Chemotactic Peptides (fCP):

Schifmann et al., (1975) have shown that chemotaxis (migration of cells toward a gradient of a chemoattractant molecule) of phagocytic cells is induced by short-chain N-formyl-methionyl peptides active at extremely low concentrations (e.g., $10^{-9}$-$10^{-10}$ M) and referred to as formyl chemotactic peptides (fCP). Phagocytic cells contain specific receptors that bind the formyl Met-Leu-Phe (SEQ ID NO:1) peptide (fCP) with relatively high affinity, whereas the affinity of the desformyl derivative (dfCP) to the receptor is two orders of magnitude smaller (Freer et al., 1980, 1982). The fCP also induce degranulation of polymorphonuclear leukocytes (PMN) and cause the release of antimicrobial agents in the surrounding milieu (Becker, 1976; Niedel and Cuatrecasas, 1980). Most importantly, it has been shown that the formyl chemotactic peptide, when immobilized on particles, greatly enhances their phagocytosis by PMN (Becker, 1976).

SUMMARY OF THE INVENTION

While reducing the present invention to practice, it was found that a conjugate of a bacterial outer membrane binding peptide, such as a polymyxin derivative or a polymyxin analog, e.g., a polymyxin B-derived peptide, and a chemotactic peptide, such as formyl chemotactic peptide, has an improved anti-bacterial activity when acting alone and/or when administered together with a conventional antibiotic, because of the combination of bacterial binding and sensitization activities of the bacterial outer membrane binding peptide and the chemotactic activity of the chemotactic peptide, which act in synergy, via independent mechanisms, at killing and/or eradicating bacteria.

Hence, according to one aspect of the present invention there is provided a compound comprising a bacterial outer membrane binding peptide conjugated to an immune cells chemotactic peptide.

According to another aspect of the present invention there is provided a pharmaceutical composition for treatment of bacteremia and/or septicemia following infection by gram negative bacteria comprising, as an active ingredient a compound which comprises a bacterial outer membrane binding peptide conjugated to an immune cells chemotactic peptide.

According to still further features in the described preferred embodiments the pharmaceutical composition further comprising a pharmaceutically acceptable carrier.

According to still further features in the described preferred embodiments, the pharmaceutical composition further comprising a conventional antibiotic compound.

According to yet another aspect of the present invention there is provided a method of treating bacteremia and/or septicemia following infection by gram negative bacteria, the method comprising administering to a subject in need thereof a therapeutically effective amount of a compound which comprises a bacterial outer membrane binding peptide conjugated to an immune cells chemotactic peptide.

According to still further features in the described preferred embodiments the method further comprising administering a conventional antibiotic compound.

According to still further features in the described preferred embodiments the conventional antibiotic compound is selected from the group consisting of novobiocin, erythromycin, lincomycin, nafcillin, naladixic acid, rifabutin, rifampin, fusidic acid and vancomycin.

According to further features in preferred embodiments of the invention described below, the compound has a bacterial sensitization activity.

According to still further features in the described preferred embodiments the bacterial outer membrane binding peptide is a polymyxin derivative or a polymyxin analog.

According to still further features in the described preferred embodiments the immune cells chemotactic peptide is a selected from the group consisting of formyl chemotactic peptide, desformyl chemotactic peptide, chemotactic peptide with a urea derivative and tuftsin.

According to still further features in the described preferred embodiments the compound has the formula:

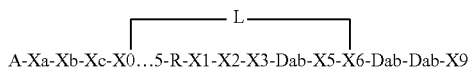

A-Xa-Xb-Xc-X0...5-R-X1-X2-X3-Dab-X5-X6-Dab-Dab-X9 wherein
X1 is a Thr or Ser residue or a covalent bond;
X2 is selected from the group consisting of Dab and Ser
X3 is selected from the group consisting of Lys, Orn, Dap, Glu, Asp, Dab and Cys residues;
X5 is a hydrophobic amino acid residue;
X6 is a hydrophobic amino acid residue;
X9 is selected from the group consisting of Ser, Tyr, Thr, Dab, Lys, Orn, Dap, Glu, Asp, Cys and n-butiric acid residues;
L is a peptide cyclization linker moiety;
R is selected from the group consisting of a covalent bond, an amino acid residue, a stretch of amino acid residues, an amino fatty acid residue having 1-12 carbon atoms in its carbon backbone and polyethylene glycol derivative;
Xa is a hydrophobic linear amino acid residue;
Xb is selected from the group consisting of linear and branched aliphatic amino acid residues;
Xc is an aromatic amino acid residue;
A is selected from the group consisting of formyl and Z-NHCONH-, where Z is n-butyl, phenyl, 4-chlorophenyl, 4-methoxyphenyl or p-tolyl derivative;
X0 . . . 5 is a stretch of 0-5 amino acid residues;
with the provisions that the A-Xa-Xb-Xc-X0 . . . 5 has an immune cells chemotactic activity and that the

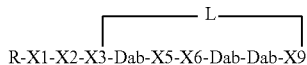

R-X1-X2-X3-Dab-X5-X6-Dab-Dab-X9 has a bacterial outer membrane binding activity.

According to still further features in the described preferred embodiments X5 is selected from the group consisting of DPhe, DTrp, DLeu, DNle, DMet, DNva and DVal residues.

According to still further features in the described preferred embodiments X5 is selected from the group consisting of Phe, Trp, Leu, Nle, Met, Nva and Val residues.

According to still further features in the described preferred embodiments X6 is selected from the group consisting of Leu, Thr, Nva, Val, Met and Ile residues.

According to still further features in the described preferred embodiments the stretch of amino acid residues is selected from the group consisting of an oligoAla stretch, an oligoAla strech interupted by at least one Glu and/or Asp residues an oligoGly strech and an oligoGly strech interupted by at least one Glu and/or Asp residues.

According to still further features in the described preferred embodiments the amino fatty acid residue is HN(CH2)xCOOH, where x is 1-12.

According to still further features in the described preferred embodiments the amino fatty acid residue is selected from the group consisting of aminocaproic acid residue and aminobutyric acid residue.

According to still further features in the described preferred embodiments the cyclization linker moiety is selected from the group —(CH2)x—NH—CO—, —(CH2)x—NH—CO—(CH2)y, CO—NH—(CH2)x, —CH$_2$—S—CH$_2$—CO— and —S—S—, where x and y are each independently 1-12.

According to still further features in the described preferred embodiments the hydrophobic linear amino acid residue is selected from the group consisting of Met and Nle.

According to still further features in the described preferred embodiments the linear and branched aliphatic amino acid residue is selected from the group consisting of Leu, Ala, Abu, Nva, Val, Ile, Cys(Me), Met and Nle.

According to still further features in the described preferred embodiments the stretch of 0-5 amino acid residues is selected from the group consisting of Phe, Ile, Nle-Tyr-Lys and DLeu-Phe-DLeu-Phe residues.

According to still further features in the described preferred embodiments Xc is selected from the group consisting of Phe residue, N-methyl derivative, 2-oxy-3-phenylpropionic acid derivative and 2-aminoxy-3-phenylpropionic acid derivative.

According to still further features in the described preferred embodiments the A-Xa-Xb-Xc-X0 . . . 5- is selected from the group consisting of:
Formyl-Met-Leu-Phe-Phe-(SEQ ID NO: 13)
Formyl-Met-Leu-Phe-Ile-(SEQ ID NO: 14)
Formyl-Nle-Leu-Phe-Nle-Tyr-Lys-(SEQ ID NO: 15)
Z-NH-CO-NH-Phe-DLeu-Phe-DLeu-Phe-(SEQ ID NO: 16)
Formyl-Met-Leu-Phe-Lys-(SEQ ID NO: 17)
Formyl-Met-Leu-N-methyl-Phe-(SEQ ID NO: 18)
Formyl-Met-Leu-2-oxy-3-phenylpropionic acid-(SEQ ID NO: 19) and
Formyl-Met-Leu-2-aminoxy-3-phenylpropionic acid-(SEQ ID NO: 20).

According to still further features in the described preferred embodiments the compound has the formula:

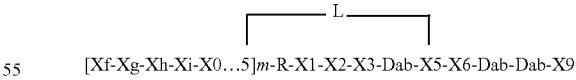

[Xf-Xg-Xh-Xi-X0...5]$m$-R-X1-X2-X3-Dab-X5-X6-Dab-Dab-X9 wherein
X1 is a Thr or Ser residue or a covalent bond;
X2 is selected from the group consisting of Dab and Ser
X3 is selected from the group consisting of Lys, Orn, Dap, Glu, Asp, Dab and Cys residues;
X5 is a hydrophobic amino acid residue;
X6 is a hydrophobic amino acid residue;
X9 is selected from the group consisting of Ser, Tyr, Thr, Dab, Lys, Orn, Dap, Glu, Asp, Cys and n-butiric acid residues;

L is a peptide cyclization linker moiety;

R is selected from the group consisting of a covalent bond, an amino acid residue, a stretch of amino acid residues, an amino fatty acid residue having 1-12 carbon atoms in its carbon backbone and polyethylene glycol derivative;

Xf is selected from the group consisting of Thr, Leu, Gly and Val residues;

Xg is selected from the group consisting of Lys and Arg residues;

Xh is selected from the group consisting of Pro, Sar and N-methyl non-polar aliphatic amino acid residues;

Xi is selected from the group consisting of Arg and Lys residues;

X0 . . . 5 is 0-5 amino acid residues;

m is an integer selected from the group consisting of 1-8, whereby if m is greater than 1 [Xf-Xg-Xh-Xi-X0 . . . 5]m is a branched structure;

with the provisions that the [Xf-Xg-Xh-Xi-X0 . . . 5]m has an immune cells chemotactic activity and that the

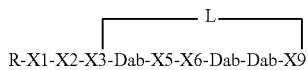

has a bacterial outer membrane binding activity.

According to still further features in the described preferred embodiments [Xf-Xg-Xh-Xi-X0 . . . 5]m- is selected from the group consisting of:

Thr-Lys-Pro-Arg-(SEQ ID NO:21)
Thr-Arg-Pro-Lys-(SEQ ID NO:22)
Leu-Lys-Pro-Arg-(SEQ ID NO:23)
Leu-Arg-Pro-Lys-(SEQ ID NO:24)
Gly-Lys-Pro-Arg-(SEQ ID NO:25)
Gly-Arg-Pro-Lys-(SEQ ID NO:26)
Val-Lys-Pro-Arg-(SEQ ID NO:27)
Val-Arg-Pro-Lys-(SEQ ID NO:28)

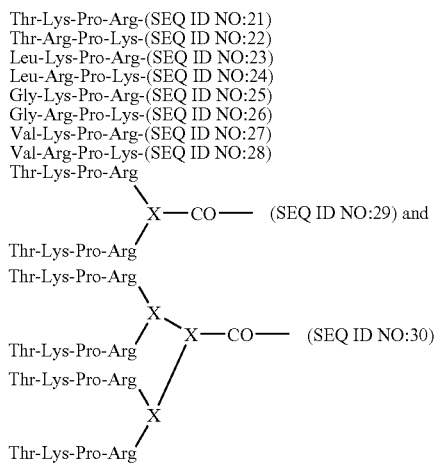

where X is selected from the group consisting of Dap, Lys and Orn residues.

According to still further features in the described preferred embodiments the compound is selected from the group consisting of SEQ ID NOs: 2, 4 and 6-11.

The present invention successfully addresses the shortcomings of the presently known configurations by providing new therapeutics highly effective in the treatment of bacteremia and septicemia.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
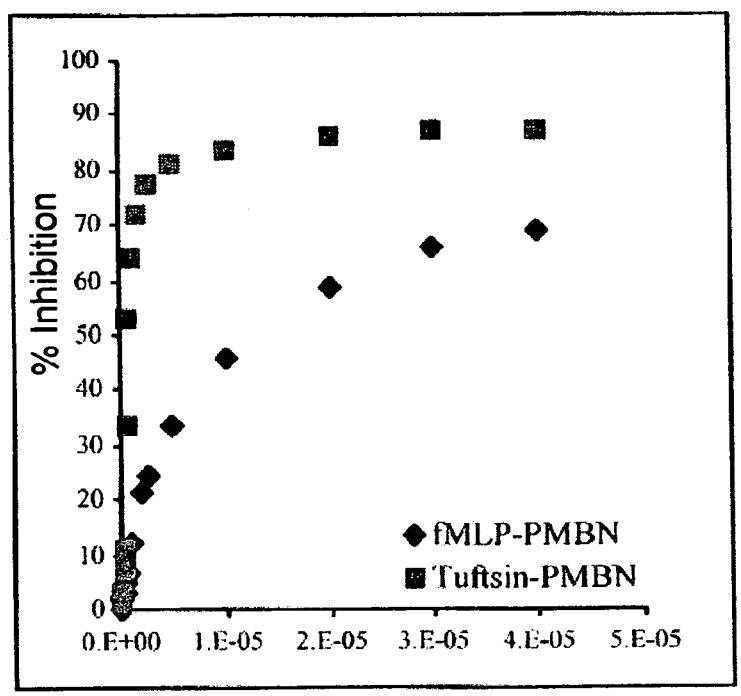
FIG. 1 is a graph showing displacement curves of Dansyl-PMBN with tuftsin-PMBN and fMLF-PMBN. Peptides were added to E. coli LPS solution (3 μg/mL) bound to dansyl-PMBN (0.55 μM). The fluorescence inhibition was measured 5 minutes after each addition at excitation and emission wavelengths of 340 and 485 nm, respectively.

The present invention is of compounds, pharmaceutical compositions and methods which can be used in the treatment of bacteremia and septicemia. Specifically, the present invention is of novel conjugates of bacterial outer membrane binding peptides, preferably having bacterial sensitization activity, and immune cells chemotactic peptides, and pharmaceutical compositions containing same, useful in the treatment of bacteremia and/or septicemia following infection by gram negative bacteria administered alone or in combination with conventional antibiotics.

The principles and operation of the compounds, compositions and therapeutic methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Bacteremia infections caused by various bacteria species and by gram negative bacilli in particular constitute one of the major, if not the principal, problem related to infection diseases encountered in modern medical centers. Antibiotic treatment is often administrated at late stages of the disease, usually when symptoms appear. The extended time required by the antibiotic to kill the pathogen is often not sufficient to prevent tissue damage. Moreover, in many cases the antibiotic is given before performing adequate sensitivity tests to determine the type of antibiotic toward which the pathogen is sensitive. In the case of gram negative infections, there is an increasing probability that the invading strain of bacteria is resistant to such "blind" antibiotic treatment. These are the main reasons for the high mortality rate due to bacterial-septicemia, in spite of antibiotic treatment.

While reducing the present invention to practice, it was found that a conjugate of a bacterial outer membrane binding peptide, such as a polymyxin derivative or a polymyxin analog, e.g., a polymyxin B-derived peptide, and a chemotactic peptide, such as formyl chemotactic peptide, has an improved anti-bacterial activity when acting alone and/or when administered together with a conventional antibiotic, because of the combination of bacterial binding and sensitization activities of the bacterial outer membrane binding peptide and the chemotactic activity of the chemotactic peptide, which act in synergy, via independent mechanisms, at killing and/or eradicating bacteria.

Hence, according to one aspect of the present invention there is provided a compound comprising a bacterial outer membrane binding peptide, which preferably has also a bacterial sensitization activity, conjugated to an immune cells chemotactic peptide.

According to another aspect of the present invention there is provided a pharmaceutical composition for treatment of bacteremia and/or septicemia following infection by gram negative bacteria comprising, as an active ingredient a compound which comprises a bacterial outer membrane binding peptide conjugated to an immune cells chemotactic peptide. The pharmaceutical composition preferably further comprising a pharmaceutically acceptable carrier.

In a preferred embodiment of the invention, the pharmaceutical composition further comprising a conventional antibiotic compound, preferably, a hydrophobic antibiotic compound, such as, but not limited to, novobiocin, erythromycin, lincomycin, nafcillin, naladixic acid, rifabutin, rifampin, fusidic acid and vancomycin.

According to yet another aspect of the present invention there is provided a method of treating bacteremia and/or septicemia following infection by gram negative bacteria, the method comprising administering to a subject in need thereof a therapeutically effective amount of a compound which comprises a bacterial outer membrane binding peptide conjugated to an immune cells chemotactic peptide. In a presently preferred embodiment of the invention, the method further comprising co-administering a conventional is antibiotic compound, examples of which are provided herein above.

In one example, the bacterial outer membrane binding peptide is a polymyxin derivative or a polymyxin analog.

In one example, the immune cells chemotactic peptide is formyl chemotactic peptide, desformyl chemotactic peptide, chemotactic peptide with a urea derivative and tuftsin.

As used herein the term "peptide" includes native peptides (either degradation products or synthetically synthesized peptides) and further to peptidomimetics, such as peptoids and semipeptoids which are peptide analogs, which may have, for example, modifications rendering the peptides more stable while in a body, having lower immugenicity and/or higher affinity to their receptors.

The term "conjugate" is used herein to describe a chimeric moiety including at least two peptides covalently linked to one another directly or via a linker, via any bond type including a peptide bond. A conjugate can be prepared synthetically using solid phase techniques as a whole, or a conjugate can be prepared by covalently joining a first peptide to a second peptide post synthesis of the first and second peptides, Modifications in peptides include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified in Quantitative Drug Design, C. A. Ramsden Gd., Chapter 17.2, F. Choplin Pergamon Press (1992), which is incorporated by reference as if fully set forth herein. Further detail in this respect are provided hereinunder.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine.

Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations.

Further elaboration of the possible amino acids usable according to the present invention and examples of non-natural amino acids are given hereinunder.

Hydrophilic aliphatic non-charged natural amino acids such as Ala, Val, Leu, Ile, Gln, Thr, Ser, Cys can in many cases be substituted with non-natural hydrophilic aliphatic non-charged amino acid (examples being norleucine (Nle), nor-valine (Nva), α-aminobutyric acid). Hydrophilic aliphatic natural amino acids can in many cases be substituted by synthetic amino acids, preferably Nleu, Nval and/or α-aminobutyric acid. Amino acids of the general formula —HN$(CH_2)_n$COOH, wherein n=3-5, as well as branched derivatives thereof, such as, but not limited to,

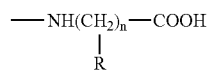

wherein R is, for example, methyl, ethyl or propyl, located at any one or more of the n carbons can also be used.

Natural positively charged amino acids can in many cases be substituted by positively charged aliphatic carboxylic acids, such as, but not limited to, $H_2N(CH_2)_n$COOH, wherein n=2-4 and $H_2N$—C(NH)—NH$(CH_2)_n$COOH, wherein n=2-3, as well as by hydroxy Lysine, N-methyl Lysine or ornithine (Orn).

Natural aromatic amino acids can be substituted by enlarged aromatic residues, such as, but not limited to, $H_2N$—$(C_6H_6)$—$CH_2$—COOH, p-aminophenyl alanine, $H_2N$—F(NH)—NH—$(C_6H_6)$—$CH_2$—COOH, p-guanidinophenyl alanine or pyridinoalanine (Pal).

Amino acid residues having a side-chain, such as, OH, SH or $NH_2$, like Ser, Tyr, Lys, Cys or Orn, can be derivatized by alkyl, aryl, alkanoyl or aroyl. In addition, OH groups may also be derivatized by phosphorylation and/or glycosylation.

Cyclic amino acid derivatives can be used. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N$((CH_2)_n$—COOH)—C(R)H—COOH or H—N$((CH_2)_n$—COOH)—C(R)H—$NH_2$, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—$CH_2$—)$_n$—S—$CH_2$—CO—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted by N-methylated bonds (—N(CH$_3$)—CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom.

Natural aromatic amino acids, Trp, Tyr and Phe, may be substituted for synthetic non-natural acid such as TIC, naphthylalanine, ring-methylated derivatives of Phe, halogenated derivatives of Phe or o-methyl-Tyr.

Tables 1-2 below list all of the naturally occurring amino acids (Table 1) and some of the non-conventional or modified amino acids (Table 2).

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |

TABLE 2-continued

| Non-conventional amino acid | Code |
|---|---|
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |

TABLE 2-continued

| Non-conventional amino acid | Code |
|---|---|
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α-methylvaline | Mtrp |
| L-α-methylleucine | Mval |
|  | Nnbhm |
| N-(N-(2,2-diphenylethyl) carbamylmethyl-glycine | Nnbhm |
| 1-carboxy-1-(2,2-diphenyl ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgin |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl) glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |

TABLE 2-continued

| Non-conventional amino acid | Code |
|---|---|
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl(1)glycine | Nnbhe |

A peptide conjugate or compound of the invention can be administered per se or as an active ingredient in a pharmaceutical composition which may further include additional active ingredients such as an antibiotic and/or a pharmaceutically acceptable carrier.

As used herein a "pharmaceutical composition" refers to a preparation of one or more of the conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of lactic acid.

In this respect, it should be pointed out that some of the conjugates of the present invention, according to preferred embodiments, are readily soluble in aqueous media and are therefore easily formulated.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the conjugates of the invention may be formulated in aqueous solutions, preferably in physiologically compatible buffers such as Hank's solution, Ringer's solution, or physiological saline buffer with or without organic solvents such as propylene glycol, polyethylene glycol and the like. For transmucosal administration, penetrants are used in the formulation. Such penetrants are generally known in the art.

For oral administration, the conjugates can be formulated readily by combining the active compounds with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as aqueous solution, fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the conjugates are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The conjugates described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the conjugates to allow for the preparation of highly concentrated solutions.

Alternatively, the active ingredient may be in powder form for constitution with a suitable vehicle, e.g., sterile, pyrogen-free water, before use.

The conjugates of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of conjugate effective to prevent, alleviate or ameliorate symptoms of pathology or prolong the survival of the subject being treated.

Determination of a therapeutically effective amount is well within the capability of those skilled in the art, especially in light of the detailed disclosure provided herein.

For any conjugate used in the methods of the invention, the therapeutically effective amount or dose can be estimated initially from activity assays in cell cultures and/or animals. For example, a dose can be formulated in animal models to achieve a circulating concentration range that includes the $IC_{50}$ as determined by activity assays (e.g., the concentration of the test compound, which achieves a half-maximal inhibition). Such information can be used to more accurately determine useful doses in humans.

Toxicity and therapeutic efficacy of the conjugates described herein can be determined by standard pharmaceutical procedures in experimental animals, e.g., by determining the $IC_{50}$ and the $LD_{50}$ (lethal dose causing death in 50% of the tested animals) for a subject conjugate. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data, e.g., the concentration necessary to achieve 50-90% inhibition may be ascertained using the assays described herein. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as a U.S. Food and Drug Administration (FDA) approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a conjugate of the invention formulated in a compatible pharmaceutical carrier may also be prepared, placed in an appropriate container, and labeled for treatment of an indicated condition, such as bacteremia and/or septicemia.

In one embodiment the compound (conjugate) of the present invention has the formula:

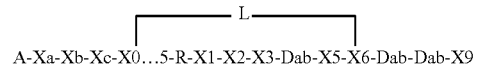

wherein
 X1 is a Thr or Ser residue or a covalent bond;
 X2 is selected from the group consisting of Dab and Ser
 X3 is selected from the group consisting of Lys, Orn, Dap, Glu, Asp, Dab and Cys residues;
 X5 is a hydrophobic amino acid residue;
 X6 is a hydrophobic amino acid residue;
 X9 is selected from the group consisting of Ser, Tyr, Thr, Dab, Lys, Orn, Dap, Glu, Asp, Cys and n-butiric acid residues;
 L is a peptide cyclization linker moiety;
 R is selected from the group consisting of a covalent bond, an amino acid residue, a stretch of amino acid residues, an amino fatty acid residue having 1-12 carbon atoms in its carbon backbone and polyethylene glycol derivative;
 Xa is a hydrophobic linear amino acid residue;
 Xb is selected from the group consisting of linear and branched aliphatic amino acid residues;
 Xc is an aromatic amino acid residue;
 A is selected from the group consisting of formyl and Z-NHCONH-, where Z is n-butyl, phenyl, 4-chlorophenyl, 4-methoxyphenyl or p-tolyl derivative;
 X0 . . . 5 is a stretch of 0-5 amino acid residues;
 with the provisions that the A-Xa-Xb-Xc-X0 . . . 5 has an immune cells chemotactic activity and that the

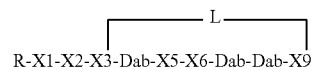

has a bacterial outer membrane binding activity.

X5 can be a DPhe, DTrp, DLeu, DNle, DMet, DNva or a DVal residue.

X5 can also be a Phe, Trp, Leu, Nle, Met, Nva or a Val residue.

According to still further features in the described preferred embodiments X6 is selected from the group consisting of Leu, Thr, Nva, Val, Met and Ile residues.

The stretch of amino acid residues can be, for example, an oligoAla stretch, an oligoAla strech interupted by at least one Glu and/or Asp residues an oligoGly strech and an oligoGly strech interupted by at least one Glu and/or Asp residues.

The amino fatty acid residue is preferably $HN(CH2)xCOOH$, where x is 1-12. Alternatively, the amino fatty acid residue is aminocaproic acid residue or aminobutyric acid residue.

The cyclization linker moiety is preferably —(CH2)x—NH—CO—, —(CH2)x—NH—CO—(CH2)y, CO—NH—(CH2)x, —CH$_2$—S—CH$_2$—CO— and —S—S—, where x and y are each independently 1-12.

The hydrophobic linear amino acid residue is preferably Met or Nle.

The linear and branched aliphatic amino acid residue is preferably Leu, Ala, Abu, Nva, Val, Ile, Cys(Me), Met or Nle.

The stretch of 0-5 amino acid residues is preferably Phe, Ile, Nle-Tyr-Lys or DLeu-Phe-DLeu-Phe residues.

Xc is preferably Phe residue, N-methyl derivative, 2-oxy-3-phenylpropionic acid derivative or 2-aminoxy-3-phenylpropionic acid derivative.

The A-Xa-Xb-Xc-X0 . . . 5- is preferably:
Formyl-Met-Leu-Phe-Phe-(SEQ ID NO: 13)
Formyl-Met-Leu-Phe-Ile-(SEQ ID NO: 14)
Formyl-Nle-Leu-Phe-Nle-Tyr-Lys-(SEQ ID NO: 15)
Z-NH-CO-NH-Phe-DLeu-Phe-DLeu-Phe-(SEQ ID NO: 16)
Formyl-Met-Leu-Phe-Lys-(SEQ ID NO: 17)
Formyl-Met-Leu-N-methyl-Phe-(SEQ ID NO: 18)
Formyl-Met-Leu-2-oxy-3-phenylpropionic acid-(SEQ ID NO: 19) or
Formyl-Met-Leu-2-aminoxy-3-phenylpropionic acid-(SEQ ID NO: 20)

According to a second embodiment the compound of the present invention has the formula:

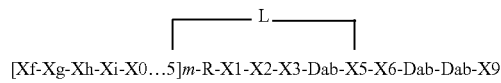

wherein

X1 is a Thr or Ser residue or a covalent bond;

X2 is selected from the group consisting of Dab and Ser

X3 is selected from the group consisting of Lys, Orn, Dap, Glu, Asp, Dab and Cys residues;

X5 is a hydrophobic amino acid residue;

X6 is a hydrophobic amino acid residue;

X9 is selected from the group consisting of Ser, Tyr, Thr, Dab, Lys, Orn, Dap, Glu, Asp, Cys and n-butiric acid residues;

L is a peptide cyclization linker moiety;

R is selected from the group consisting of a covalent bond, an amino acid residue, a stretch of amino acid residues, an amino fatty acid residue having 1-12 carbon atoms in its carbon backbone and polyethylene glycol derivative;

Xf is selected from the group consisting of Thr, Leu, Gly and Val residues;

Xg is selected from the group consisting of Lys and Arg residues;

Xh is selected from the group consisting of Pro, Sar and N-methyl non-polar aliphatic amino acid residues;

Xi is selected from the group consisting of Arg and Lys residues;

X0 . . . 5 is 0-5 amino acid residues;

m is an integer selected from the group consisting of 1-8, whereby if m is greater than 1 [Xf-Xg-Xh-Xi-X0 . . . 5]m is a branched structure;

with the provisions that the [Xf-Xg-Xh-Xi-X0 . . . 5]m has an immune cells chemotactic activity and that the

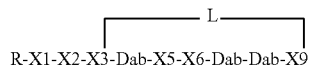

has a bacterial outer membrane binding activity.

Thr-Lys-Pro-Arg-(SEQ ID NO:21)
Thr-Arg-Pro-Lys-(SEQ ID NO:22)
Leu-Lys-Pro-Arg-(SEQ ID NO:23)
Leu-Arg-Pro-Lys-(SEQ ID NO:24)
Gly-Lys-Pro-Arg-(SEQ ID NO:25)
Gly-Arg-Pro-Lys-(SEQ ID NO:26)
Val-Lys-Pro-Arg-(SEQ ID NO:27)
Val-Arg-Pro-Lys-(SEQ ID NO:28)

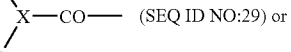

where X is selected from the group consisting of Dap, Lys and Orn residues.

Exemplary compounds of the present invention are those identified by SEQ IS NOs:2, 4 and 6-11.

Specific and general methods of synthesizing compounds in accordance with the teachings of the present invention are provided in the Examples section below. Such compounds can be tested for toxicity and efficacy using one or more of the in vivo and in vitro assays described in the Examples section that follows. For example, the displacement assay can provide data regarding the affinity of a tested compound to gram negative bacteria, the sensitization assay can provide data regarding the sensitization activity of a tested compound, the minimal inhibitory concentration (MIC) assay, the phagocytosis activity assay and the mice protection assay can provide data regarding the therapeutic efficacy of a tested compound, the efficacy against clinical isolates assay can provide data regarding the range of efficacy of a tested compound, whereas the toxicity assay can provide data regarding the toxicity of a tested compound.

The present invention provides new therapeutics highly effective in the treatment of bacteremia and septicemia. The compounds of the present invention enhance killing and eradication of bacteria in the blood and other body fluids and organs and is highly suitable in treating primary severe invasive infections caused by gram-negative bacteria. Other infections by gram negative bacteria are also treatable by the compounds of the present invention.

The compounds of the present invention have certain activities which synergistically complement one another. These activities include: binding to the outer membrane of gram negative bacteria; sensitization of gram negative bacteria, rendering such bacteria susceptible to conventional antibiotics and anti-bacterial agents secreted from immune cells; chemotaxis of phagocytic cells which are capable of eradicating gram negative bacteria and of secreting anti-bacterial agents; and signaling to phagocytic cells to secrete anti-bacterial agents. Taken together, these activities result in highly efficient treatment of bacteremia and/or septicemia following infection by gram negative bacteria Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

General Peptide Conjugate Synthesis

Linear peptide chains are assembled by conventional solid phase synthesis, using an automated solid phase multiple peptide synthesizer. Fmoc-strategy is employed throughout the peptide-chain assembly using orthogonal protecting groups. Cyclization is performed in solution as described above for amide bond formation. Cyclization through S—S bridge is achieved by air oxidation. Final deprotection is achieved either by TFA:TMSBr:thioanisol:ethandithiol:m-cerasol (58:10:19:10:3, v:v:v:v:v) at 0° C., for 1 hour, or by catalytic (Pd/C) hydrogenation in acetic acid: methanol:water (5:4:1, v:v:v).

Example 2

Synthesis of PMBN Conjugates: [fMLF]PMBN and [MLF]PMBN

Linear peptide chains were assembled by conventional solid phase synthesis, using an ABIMED AMS-422 automated solid phase multiple peptide synthesizer (Langenfeld, Germany). Fmoc-strategy was employed throughout the peptide-chain assembly following the company's protocol. Synthesis was initiated by using Fmoc-Thr(tBu)-Wang resin (0.4 mmol/1 g) and was performed on a 25 μmol-scale. Side-chain amino protecting groups for 2,4-diaminobutyric acid (Dab) were tert-butyloxycarbonyl (tBoc) and benzyloxycarbonyl (Cbz). Fmoc-D-Phe-OH, Fmoc-Leu-OH, Fmoc-Thr(tBu)-OH and Fmoc-Met-OH were used as building units. Coupling was achieved using 4 equivalents of benzotriazole-1-yl-oxy-tris-pyrolidino-phosphonium hexafluorophosphate (PyBOP) as a coupling agent and 8 equivalents of 4-methylmorpholine (NMM), all dissolved in dimethylformamide (DMF). The fully protected peptide-bound resin was treated with piperidine (20% in DMF) for 20 minutes, then washed (DMF) and the free N-terminus amino moiety reacted with 4 equivalents of Cbz-OSu (for [MLF]PMBN) or 2,4,5-Trichlorophenyl formate (for [fMLF]PMBN) and 4 equivalents of N,N-diisopropylethylamine (DIEA) in DMF for 3 hours. The fully protected peptide-bound resin was treated with trifluoroacetic acid (TFA):water:triethylsilane (TES) (95:2.5:2.5; v:v:v) for 1 hour at room temperature and filtered. The solution containing the cleavage mixture was cooled to 4° C. and the partially protected linear peptide was precipitated with ice-cold di-tert-butyl methyl ether:petroleum ether (30-40° C.) (1:3, v:v) and centrifuged. The pellet was washed with the same mixture and dissolved in water:acetonitrile (2:3, v:v) and lyophilized.

Cyclization was then performed in DMF at peptide concentration of 1 mM using PyBOP:1-hydroxybenzotriazole (HOBT):NMM (4:4:8, equivalents) as reagents for 2 hours at room temperature. The yield was over 95% according to analytical HPLC. The reaction mixture was concentrated in high vacuum and the cyclic peptidic product was precipitated by treatment with water. Final deprotection, i.e., removal of Cbz, was achieved by catalytic (Pd/C) hydrogenation in acetic acid: methanol:water (5:4:1, v:v:v). The synthesis of [fMLF]PMBN is schematically described in Scheme 1, below.

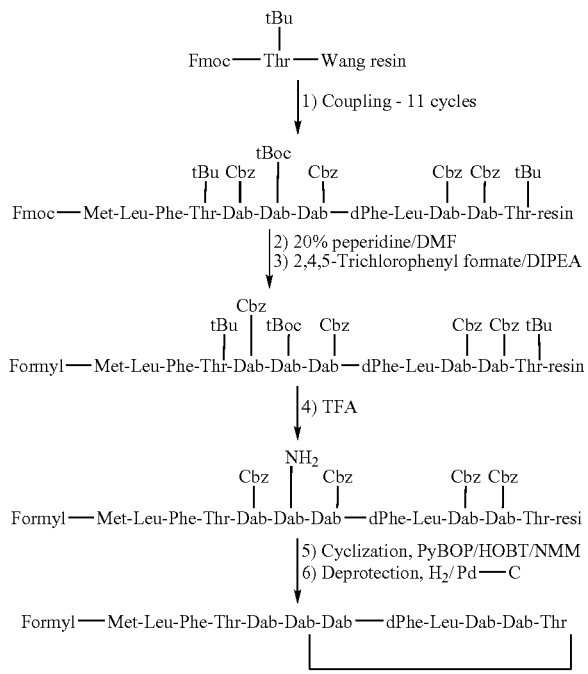

Example 3

Synthesis of PMBN Conjugates: [Tuftsin]PMBN

As described for [MLF]PMBN when Fmoc-Lys(Cbz)-OH, Fmoc-Arg(Pbf)-OH and Fmoc-Pro-OH were used as building unit.

Final peptide deprotection was achieved with mixture of TFA:TMSBr:thioanisol:ethandithiol:m-cerasol (58:10:19:10:3, v:v:v:v:v) at 0° C., for 1 hour. The peptide was precipitated by the addition of cold tert-butylmethyl ether, centrifuged, washed with cold tert-butylmethyl ether and lyophilized from water.

Example 4

General Branched Peptide Conjugate Synthesis

A linear peptide is synthesized as described above. After the completion of assembly of the linear bacteria binding peptide the elongation with the branched part is prepared using 2-3 coupling cycles using Fmoc-Lys(Fmoc)-OH or Fmoc-Orn(Fmoc)-OH or Fmoc-Dap(Fmoc)-OH. Then the linear chemotactic peptides are built up on the branced template using the linear peptide synthesis as described above.

Example 5

Peptides cyclization via disulfid bond (S—S) is performed using air oxidation which is ledding to formation of intramolecular disulfide bridge. Thus, each peptide is dissolved in high dilution (1 mg/5 ml) in ammonium acetate buffer (pH 7-8) and the solution is stirred at room temperature for 24-48 hours.

Example 6

Experimental Procedures

1. Displacement Assay:

To determine the binding of a given peptide to LPS, a displacement assay was performed in which 5 or 10 μl ($1 \times 10^{-5}$-$1 \times 10^{-3}$ M) of the tested peptide at desired concentrations were added at 5 minutes interval to a pre-equilibrated mixture of LPS solution (2 mL, 3 μg/mL, $\sim 2 \times 10^{-7}$ M) in HEPES buffer (5 mM, pH 7.2) and dansyl-PMBN (0.55 μM). The fluorescence intensity (excitation wavelength of 340 nm and emission wavelength of 485 nm) was recorded after each time interval. Each experiment was repeated 2-3 times. The percent inhibition of fluorescence intensity was plotted as a function of the peptide concentration from which the concentration required for maximal ($I_{max}$) and 50% ($IC_{50}$) displacement of the dansyl-PMBN from LPS was derived.

2. Minimal Inhibitory Concentration (MIC) Assay:

Gram-negative bacteria were grown on nutrient agar plates (Difco Laboratories, Detroit, Mich.) and kept at 4° C. An overnight culture in isotonic sensitest broth (ISB, Oxoid) was adjusted to $1 \times 10^5$ CFU/mL and inoculated into microtiter plate wells containing each 100 μL of a serial twofold dilution (1000-0.5 μg/mL) of the tested antibiotics in ISB. MIC was defined as the lowest concentration at which there was no visible bacterial growth after incubation for 20 hours at 37° C. The results are reported for 4-8 separate tests that varied by no more than one dilution.

3. Sensitization Assay:

Bacterial suspension (10 μL, $1 \times 10^5$ CFU) was inoculated into microtiter plate wells containing 100 μL of a serial two-fold dilution (1000-0.5 μg/mL) of novobiocin (Sigma) in ISB. To each well, 10 μL of the test peptide was added to a final concentration of 50 μg/mL. The fold decrease in MIC for novobiocin comparing wells with and without test peptides was calculated and designated as sensitizing activity. The relative sensitizing activity of the test peptide was calculated as percent of the sensitizing activity of 50 μg/mL pPMBN.

4. Phagocytosis Activity Assay:

The conjugates and the control peptides were incubated with *E. coli* ($10^6$ CFU/mL) prior to the contact with human monocytes-derived macrophages monolayer. After 30 minutes of phagocyte-bacteria encounter, the phagocytes were washed, lysed and the released bacteria allowed to grow for 4.5 hours at 37° C. The amount of trapped bacteria were calculated as a function of absorbency at 600 nm.

5. Mice Protection Assay:

Sublethal dose of *Klebsiella pneumoniae* ($2 \times 10^5$ cfu) were injected intreperitonially to mice. Four hours later, mice were treated by a mixture of the tested peptide (4 mg/kg) with erythromycin (10 mg/kg). 24 hours after the inoculation, the infected mice were treated twice with half of the dose (2 and 5 mg/Kg of peptide and erythromycin, respectively) at an interval of 4 hours. After additional 24 hours, the mice were treated once with half dose. Survival was followed daily for 7 days.

6. Toxicity Assay:

Groups of six and ten male mice (CD1, four- to six-week old, 30-36 g) are injected intravenously to the tail veins with peptide solution (0.2 mL in sterile DDW, 0.5 mm×16 mm needle). Survivals are monitored after one day.

Example 7

Conjugates

Synthetic chimeric molecules each consisting of a conjugate of two shorts peptides, a cyclic nona peptide capable of binding to bacterial surface and a chemotactic peptide, e.g., fMLF (SEQ ID NO:1) or tuftsin (SEQ ID NO:12) were synthesized according to the procedures described under Examples 1-5.

These conjugates were expected to possess two activities aimed at eradicating bacterial pathogen.

One activity is the ability to bind to the bacterial outer membrane, through the cyclic peptide moiety and to act as an opsonin in promoting phagocytosis of the bacteria through a chemotactic peptide moiety (e.g., fMLF or tuftsin).

The other activity is to sensitize the bacteria and render it susceptible to other antibiotics as well as to phagocytes-derived antimicrobial agents, which are released upon interaction with the conjugates.

As is shown below, compared to native polymyxin B derived peptide, the conjugate peptides exhibit improved sensitizing activity and a new indirect bactericidal activity by promoting the phagocytosis of the bacteria by human monocyte-derived macrophages.

The following Table 3 provides the structure of peptides and exemplary conjugate peptides synthesized and tested for therapeutic efficacy according to the present invention:

TABLE 3

Peptides and Conjugates

| No. | Peptide/Conjugate (SEQ ID NO:) | Sequence |
|---|---|---|
| 1 | PMBN (2) | Thr-Dab-cyclo[Dab-Dab-dPhe-Leu-Dab-Dab-Thr] |
| 2 | fMLF-PMBN (3) | Formyl-Met-Leu-Phe-Thr-Dab-cyclo[Dab-Dab-dPhe-Leu-Dab-Dab-Thr] |
| 3 | tuftsin-PMBN (4) | Thr-Lys-Pro-Arg-Thr-Dab-cyclo[Dab-Dab-dPhe-Leu-Dab-Dab-Thr] |
| 4 | PMLBO (5) | Dab-cyclo[Dab-Dab-dPhe-Leu-Dab-Dab-Thr] |
| 5 | fMLF-PMBN (6) | Formyl-Met-Leu-Phe-Dab-cyclo[Dab-Dab-dPhe-Leu-Dab-Dab-Thr] |
| 6 | (7) | H-Lys-Thr-Lys-cyclo[Cys-Lys-Phe-Leu-Lys-Lys-Cys]-OH |
| 7 | (8) | H-Thr-Lys-Pro-Arg-Lys-Thr-Lys-cyclo[Cys-Lys-Phe-Leu-Lys-Lys-Cys]-OH |
| 8 | (9) | H-Thr-Lys-Pro-Arg-Ala-Ala-Ala-Lys-Thr-Lys-cyclo[Cys-Lys-Phe-Leu-Lys-Lys-Cys]-OH |
| 9 | (10) | N-Formyl-Met-Leu-Phe-Lys-Thr-Lys-cyclo[Cys-Lys-Phe-Leu-Lys-Lys-Cys]-OH |
| 10 | (11) | N-Formyl-Met-Leu-Phe-Ala-Ala-Ala-Lys-Thr-Lys-cyclo[Cys-Lys-Phe-Leu-Lys-Lys-Cys]-OH |

Example 8

Bacterial Sensitization Activity of PMBN-chemotactic Peptide Conjugates

The conjugate peptides, PMBN-fMLF and PMBN-tuftsin (Table 3), were synthesized and characterized. Both chimeric peptides revealed no antimicrobial activity per se. However, they exhibited a most substantial increased ability to sensitize *E. coli* and *Klebsiella pneumonia* towards novobiocin. They were 2.5 to 9 times more efficient then their parent PMBN (Table 4). The increased activity was due to the addition of a "tail" at the N-terminal of PMBN. However, the addition of the relatively hydrophobic peptide formyl-Met-Leu-Phe, fMLF, to PMBN did not significantly reduce its minimal inhibitory concentration (MIC) towards *E. coli* and *Klebsiella pneumonia*. Furthermore, the ability of fMLF-PMBN to displace bound Dansyl-PMBN from LPS was even lower than PMBN (Table 4, FIG. 1).

TABLE 4

Sensitization of bacteria by peptide conjugates and their affinity to LPS

| | peptides potency (%) | | |
|---|---|---|---|
| peptide | *Escherichia coli* | *Klebsiella pneumonia* | Peptides $IC_{50}$ (μM) |
| PMBN | 100 | 100 | 4.5 |
| fMLF-PMBN | 783 | 475 | 12 |
| Tuftsin-PMBN | 863 | 268 | 0.7 |
| Polymyxin B | — | — | 0.5 |

Values were calculated as peptide's potency, at a concentration of 50 μg/ml, relatively to PMBN. $IC_{50}$ values represent peptide concentrations that inhibits 50% of the initial fluorescence of 0.55 μM Dansyl-PMBN bound to *E. coli*-LPS.

The above data clearly indicates that the fMLF portion fails to behave as the fatty acid moiety of polymyxin B. One of the aspects related to its mode of action is probably by promoting the interaction with the bacterial outer membrane but it apparently does not interact with the inner lipid A portion.

The addition of the hydrophilic peptide Thr-Lys-Pro-Arg (SEQ ID NO:12), tuftsin, to the N-terminal of PMBN did not significantly reduce its minimal inhibitory concentration (MIC) towards *E. coli* and *Klebsiella pneumonia*. However, tuftsin-PMBN exhibits increased ability to enhance the permeability of the bacterial outer membrane to novobiocin.

In addition, tuftsin-PMBN showed much higher potency then PMBN to displace Dansyl-PMBN from LPS (FIG. 1). In fact, its affinity to LPS is similar to that of native polymyxin B. The additional two positive charges (Lys and Arg) probably increased its affinity to the LPS relatively to PMBN, even though tuftsin-PMBN (like fMLF-PMBN) did not have antimicrobial activity by it self.

Compounds 6-10 (SEQ ID NOs:7-11, Table 3) were less active in the sensitization assay as compared to the parent PMBN, yet had some efficacy.

Example 9

Phagocytosis Activity of PMBN Conjugates

Tuftsin-PMBN and fMLF-PMBN were designed to enhance microbial killing by phagocyte cells like macrophages, monocytes and polymophonuclear leukocytes. The ability of both conjugates to increase phagocytosis of human monocytes derived macrophages was examined.

Figure 2:
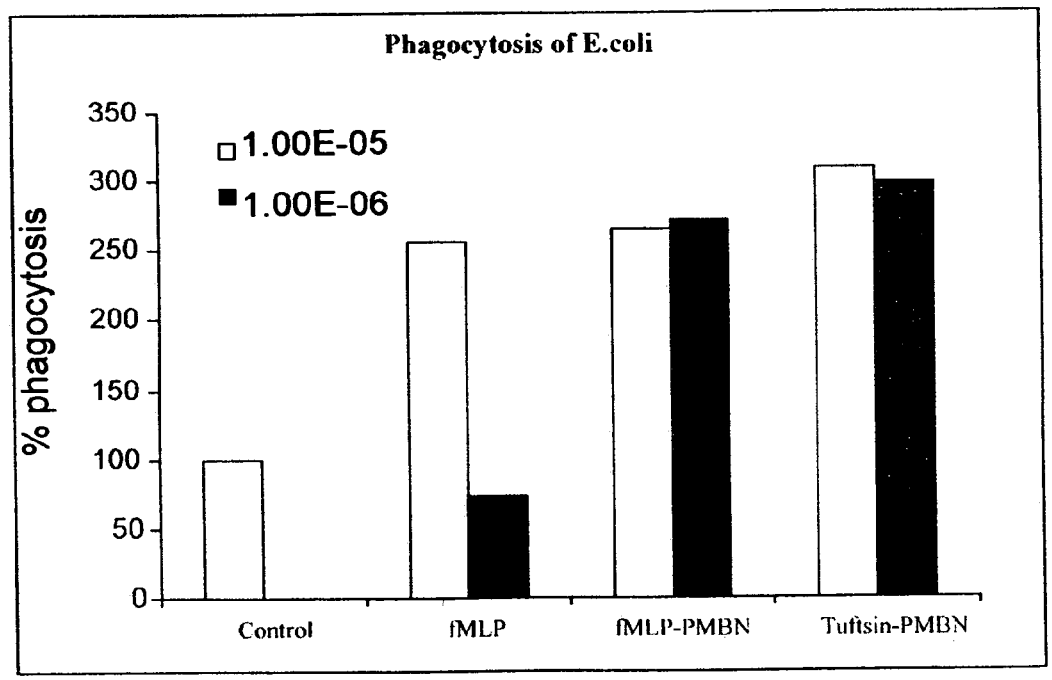
FIG. 2 is a bar graph demonstrating the enhancement of phagocytosis with conjugates peptide. Open boxes—10 μM, closed boxes—1 μM, of the respective peptides.

The conjugates and the control peptides were incubated with *E. coli* ($10^6$ CFU/mL) prior to the contact with human monocytes-derived macrophages monolayer. After 30 minutes of phagocyte-bacteria encounter, the phagocytes were washed, lysed and the released bacteria allowed to grow for 4.5 hours at 37° C. The amount of trapped bacteria were calculated as a function of absorbency at 600 nm. fMLF by itself (10 μM) enhanced by 2.5 fold the phagocytosis comparing to the control (FIG. 2). However, at lower concentration (1 μM) only fMLF-PMBN enhanced the phagocytosis of the bacteria. Tuftsin-PMBN enhanced the phagocytosis by 3 folds comparing to the control. Both conjugates exhibited increased phagocytosis of the bacteria indicating that the N-terminal segment of the bacteria-bound conjugate is free to interact with its cognate receptor on the phagocyte cell. Moreover, the addition of the cyclic large molecule to the short peptides did not reduce their affinity to the phagocyte cell.

The activity of Polymyxin B octapeptide (PMBO) and its conjugate PMBO-fMLF in sensitization and phagocytosis enhancement were similar to those of PMBN and its conjugate PMBN-fMLF, respectively.

Example 10

Protection of Mice with Peptide Conjugates

Polymyxin octapeptide conjugated with the tripeptide formyl Met-Leu-Phe (fMLF, SEQ ID NO:1) was assayed in combination with erythromycin for the ability to provide protection against *Klebsiella pneumoniae* infection in an in vivo infection model previously described (Ofek et al., 1994).

The bacteria were erythromycin resistant and thus all 18 mice who received erythromycin only died (Table 5). PMBN, which in vitro enhance the activity of erythromycin, provided partial protection. Almost complete protection, however, was obtained with the undecapeptide [fMLF]PMBN, which enhance activity of the erythromycin and enhance phagocytosis of the bacteria as well.

TABLE 5

Protective activity of polymyxin B-based peptides co-administered with erythromycin in mice challenged with erythromycin resistant ($Ert^r$) *Klebsiella pneumoniae*

| Compounds injected intraperitoneally | Dosage mg/Kg | Mice survival (Dead/Total) |
|---|---|---|
| Erythromycin | 10 | 18/18 |
| Erythromycin + PMBN | 10 + [4 + 2 + 2 + 2]* | 9/18 |
| Erythromycin + PMBO-f-MLP | 10 + [4 + 2 + 2 + 2] | 3/18 |
| Erythromycin + PMBO-f-MLF | 10 + [2 + 1 + 1 + 1] | 1/6 |
| Polymyxin B | 1.5 + 1.5 + 1.5 | 3/18 |

For dosages, see "mice protection assay" under Example 6, above.

Example 11

Tests with Clinical Isolates

In previous studies it was found that the PMBN alone renedered 53 out of 53 clinical isolates more suceptible to novobiocin (ofek et al, 1994). In similar experiments it was shown that PMBOMLP rendered 12 out of 12 clinical isolates—belonging to *Pseudomonas aeruginosa* and *Klebsiella*

*pneumoniae* significantly more susceptible to—a number of antibiotics (including erruthromycin, amikin, augmentin, zinacef and novobiocin, see Table 6, below). This data taken together suggests that the emergence of strains resistant to the binding and sensitizing activities of the conjugates of the present invention is expected to be rare.

TABLE 6

Sensitizing activity of peptide conjugates for clinical isolates of gram-negative bacteria

| Bacteria (No strains tested) | | Test agent | Range of MIC (µg/ml) |
|---|---|---|---|
| *Pseudomonas aeruginosa* | (8) | Novobiocin | 62–1000 |
| | | Novobiocin + PMBO MLP | 0.5–8 |
| | (8) | Erythromycin | 200 |
| | | Erythromycin + PMBO MLP | 1.2–2.5 |
| | (3) | Gentamycin | 1000 |
| | | Gentamycin + PMBO MLP | >200 |
| | (7) | Augmentin | 620–1250 |
| | | Augmentin + PMBO MLP | 5–160 |
| | (7) | Zinacef | 468–3750 |
| | | Zinacef + PMBO MLP | 1.5–234 |
| | (8) | Amikin | 62–160 |
| | | Amikin + PMBO MLP | 2.5–31 |
| | | Amikin + PMBO fMLP | 16–31 |
| *Klebsiella pneumoniae* | (4) | Erythromycin | 100–200 |
| | | Erythromycin + PMBO MLP | 0.1–5 |
| | | Erythromycin + PMBO fMLP | 0.2–4 |
| | (1) | Amikin | 20 |
| | | Amikin + PMBO MLP | 8 |
| | | Amikin + PMBO fMLP | 8 |

Experiments for the determining the sensitizing activity of the conjugates were performed similar to those described for PMBN in previous studies (Ofek et al 1994). All conjugates were teted at 20 µg/ml to determine the MIC of the indicated antibiotic. Antibiotics were purchased from Sigma (novobiocin, erythromycin and gentamycin), Bristol (Amikin), Galaxo (Zinacef), and B.R.L (augmentin). Numbers in brackets indicate number of is strains tested.

Example 12

Toxicity Assays

The toxicity of cyclic nonapeptide derivatives of polymyxins has been determined in a number of in vitro and in vivo assays. The $LD_{50}$ of polymyxin B or colistin in mice is in the range of 6-10 mg/Kg body weight when administered intravenously and 18-30 mg/Kg body weight when administered intraperitoneally, while that of colistin derived-peptide is 15 times less toxic (e.g., $LD_{50}$ of 150 mg/Kg body weight) than the parent molecule (Chihara et al., 1974), and doses as high as 200 mg/Kg body weight of PMBP were not lethal (Lam et al., 1986).

Furthermore, 3 mg/Kg body weight PMBP administered intravenously to dogs and rats over a long period of time did not cause neuromuscular blockade and neurotoxic or nephrotoxic effects, all of which were observed in animals administered with the same dose of polymyxin B (Danner et al., 1989).

The toxicity expressed as $LD_{50}$ of the peptide-derivatives of the present invention, when administered intravenously to mice, was 150-75 mg/Kg weight-which is about 15-10 times less than that of polymyxin B.

Hence, the addition of chemotactic peptide to PMBP had no effect on the toxicity of the molecule as compared to unconjugated PMBP.

It is evident from the in vitro and in vivo results presented herein that a bacterial outer membrane binding peptide conjugated to an immune cells chemotactic peptide act in synergy to combat bacterial infection.

The conjugate opsonize the bacteria to enhance killing and eradication by phagocytic cells and, at the same time, sensitize the bacteria to be susceptible to conventional antibiotics, even in the case where the bacteria is resistant to the conventional antibiotics of choice.

This data suggests that the conjugates of the present invention posses a great potential in clinical use for the treatment of serious blood infections caused by gram-negative bacteria.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

CITED REFERENCES

Additional References are Cited in the Text

Athamna, A. and Ofek, I. 1988. Enzyme-linked immunosorbent assay for quantitation of attachment and ingestion stages of bacterial phagocytosis. J. Clin. Microbiol. 26: 62-66.

Athamna, A., I. Ofek, Y. Keisari, S. Markowitz, G. S. Dutton and N. Sharon. 1991. Lectinophagocytosis of encapsulated *Klebsiella pneumoniae* mediated by surface lectin of guinea pig alveolar macrophages and human-monocyte-derived macrophages. Infect. Immun. 59: 1673-1682.

Becker, E. L. 1976. Some interrelations of neutrophil chemotaxis, lysosomal enzyme secretion, and phagocytosis as revealed by synthetic peptides. Amer. J. Path. 85: 385-394.

Bryan, L. E. 1982. In: Bacterial resistance and susceptibility to chemotherapeutic agents. p. 69-80. Cambridge University Press. Cambridge.

Cassel, G. H. 1995. ASM task force urges broad program on antimicrobial resistance. ASM News 61:116-120.

Chihara, S., A. Ito, M. Yhata, T. Tobita, and Y. Koyama. 1974. Chemical synthesis, isolation and characterization of a-N-fatty acyl colistin nonapeptide with special reference to the correlation between antimicrobial activity and carbon number of fatty acyl moiety. Agric. Biol. Chem. 38: 521-529.

Chihara, S., T. Tobita, M. Yhata, A. Ito, and Y. Koyama. 1973. Enzymatic degradation of colistin: isolation and identification of a-N-acyl, g-diaminobutyric acid and colistin nonapeptide. Agric. Biol. Chem. 37: 2455-2463.

Chin, G. J., and Marx, J. 1994. Resistance to antibiotics. Science 264: 359-393.

Danner, R. L., K. A. Joiner, M. Rubin, W. H. Patterson, N. Johnson, K. M. Ayers, and J. E. Parrillo. 1989. Purification, toxicity, and anti-endotoxin activity of polymyxin B nonapeptide. Antimicrob. Agents Chemother. 33:1428-1434.

Duwe, A. L., A. Rupar, G. B. Horsman, and S. I. Vas. 1986. In vitro cytotoxicity and antibiotic activity of polymyxin B nonapeptide. Antimicrob. Agents Chemother. 30: 340-341.

Freer, R. J., A. R. Day, J. A. Radding, E. Schiffman, S. Aswanikumar, H. J. Showell, and E. L. Becker. 1980. further studies on the structural requirements for synthetic peptide chemoattractants. Biochem. 19: 2404-2410.

Freer, R. J., A. R. Day, N. Muthukumaraswamy, D. Pinon, A. Wu, H. J. Showell, and E. L. Becker. 1982. Formyl peptide chemoattractants: a model of the receptor on rabbit neutrophils. Biochemistry 21: 257-263.

Kitamura-Matsunaga, H., Y. Kimura, and T. Araki. 1984. Enzymatic preparation of colistin fragments and their biological activity. Peptide Chemistry 22: 333-338.

Lam C., J. Hidebrandt, E. Schutze, and A. F. Wenzel. 1986. Membrane-disorganizing property of polymyxin B nonapeptide. J. Antimicrob. Chemother. 18:9-15.

Lambert, H. P., and F. W. O'Grade. 1992. Antibiotic and Chemotherapy. Churchill Linvingstone, Edinbutgh Metcalf, J. A. Gallin, J. I. Nauseef, W. M. and Root, R. K. 1986. Laboratory Manual of Neutrophil Function. p. 87-90 Raven Press. New York.

Morrison, D. E. and Jacobs, D. M. 1976. Binding of polymyxin B to the lipid a portion of bacterial lipopolysaccharides. Immunochemistry. 13: 813-818.

Niedel, J. E. and P. Cuatrecasas. 1980. Formyl peptide chemotactic receptors of leukocytes and macrophages. Curr. Top. in Cellular Reg. 17: 137-169.

Ofek, I. and Bekierkunst, A. Chemotactic response of leukocytes to cord factor (trehalose-6', 6'-dimicolate). J. Natl. Cancer Inst. 57:1379-1381, 1976.

Ofek, I. S. Cohen, R. Rahmani, K. Kabha, Y. Herzig and E. Rubinstein. 1994 Antibacterial synergism of polymyxin B nonapeptide and hydrophobic antibiotics in experimental gram-negative infections in mice. Ant. Microb. Agents. Chemothr. 38:374-377.

Ofek, I. Y. Goldhar, Y. Keisari, and N. Sharon. 1995. Non-opsonic phagocytosis of microorganisms. Ann. Rev Microbiol. 49: 239-276.

Rustici, A. Velucchi, M. Faggioni, R. Sironi, M. Ghezzi, P. Quataert, S. Green,B. and Porro, M. 1993. Molecular mapping and detoxification of the lipid A binding site by synthetic peptides. Science, 251: 361-365.

Schiffman, E., B. A. Coreoran, and S. M. Whal. 1975. N-Formylmethionine peptides as chemoattractants for leucocytes. Proc. Natl. Acad. Sci. USA 72: 1059-1062.

Soogard, H. 1982. The pharmacodynamics of polymyxin antibiotics with special reference to drug resistance liability. J. Vet. Pharmacol. Therap. 5: 219-231.

Vaara, M. Agents that increase the permeability of the outer membrane. 1992. Microbiol. Rev. 56: 395-411.

Vaara, M., and P. Viljanen. 1985. Binding of polymyxin B nonapeptide to gram-negative bacteria. Antimicrob. Agents Chemother. 27: 548-554.

Vaara, M., and T. Vaara. 1983. Polycations sensitize enteric bacteria to antibiotics. Antimicrob. Agents Chemother. 24∫†107-113.

Voitenko, V. G., D. I. Bayramashvili, A. I. Zebrev, and A. A. Zinchenko. 1990. Relationship between structure and histamine releasing action of polymyxin B and its analogues. Agents Actions 30: 153-156.

Young, L. S. 1985. Gram-negative sepsis. In: Principles and Practice of Infectious Diseases. G. L. Mandel, R. G. Douglas and J. E. Bennet (eds) J. Wiley & Sons, pp 452-475.

What is claimed is:

1. A compound comprising a bacterial outer membrane lipopolysaccharide-binding peptide conjugated to an immune cell chemotactic peptide, wherein said immune cell chemotactic peptide is selected from the group consisting of formyl chemotactic peptide, desformyl chemotactic peptide, chemotactic peptide with a urea derivative, and tuftsin, said outer membrane lipopolysaccharide-binding peptide and said immune cell chemotactic peptide acting in synergy to provide a bacterial sensitizing activity, wherein said formyl chemotactic peptide comprises an N-terminal N-formyl methionyl residue and said desformyl chemotactic peptide comprises an N-terminal methionyl residue.

2. The compound of claim 1, wherein said bacterial outer membrane lipopolysaccharide-binding peptide is a polymyxin derivative or a polymyxin analog.

3. A compound having the formula:

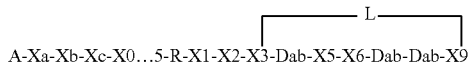

wherein

X1 is a Thr or Ser residue or a covalent bond;

X2 is selected from the group consisting of Dab and Ser;

X3 is selected from the group consisting of Lys, Orn, Dap, Glu, Asp, Dab and Cys residues;

X5 is a hydrophobic amino acid residue;

X6 is a hydrophobic amino acid residue;

X9 is selected from the group consisting of Ser, Tyr, Thr, Dab, Lys, Orn, Dap, Glu, Asp, Cys and n-butyric acid residues;

L is a peptide cyclization linker moiety;

R is selected from the group consisting of a covalent bond, an amino acid residue, a stretch of amino acid residues, an amino fatty acid residue having 1-12 carbon atoms in its carbon backbone and a polyethylene glycol derivative;

Xa is a hydrophobic linear amino acid residue;

Xb is selected from the group consisting of linear and branched aliphatic amino acid residues;

Xc is an aromatic amino acid residue;

A is selected from the group consisting of formyl and Z-NHCONH-, where Z is n-butyl, phenyl, 4-chlorophenyl, 4-methoxyphenyl or p-tolyl derivative;

X0 . . . 5 is a stretch of 0-5 amino acid residues;

with the provisions that said A-Xa-Xb-Xc-X0 . . . 5 has an immune cell chemotactic activity and that said

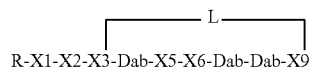

has a bacterial outer membrane lipopolysaccharide-binding activity, said immune cell chemotactic activity and said bacterial outer membrane lipopolysaccharide-binding activity acting in synergy to provide a bacterial sensitizing activity.

4. The compound of claim 3, wherein X5 is selected from the group consisting of DPhe, DTrp, DLeu, DNle, DMet, DNva and DVal residues.

5. The compound of claim 3, wherein X5 is selected from the group consisting of Phe, Trp, Leu, Nle, Met, Nva and Val residues.

6. The compound of claim 3, wherein X6 is selected from the group consisting of Leu, Thr, Nva, Val, Met and Ile residues.

7. The compound of claim 3, wherein said stretch of amino acid residues is selected from the group consisting of an oligoAla stretch, an oligoAla stretch interrupted by at least one Glu and/or Asp residue, an oligoGly stretch, and an oligoGly stretch interrupted by at least one Glu and/or Asp residue.

8. The compound of claim 3, wherein said amino fatty acid residue is HN(CH2)xCOOH, where x is 1-12.

9. The compound of claim 3, wherein said amino fatty acid residue is selected from the group consisting of aminocaproic acid residue and aminobutyric acid residue.

10. The compound of claim 3, wherein said cyclization linker moiety is selected from the group consisting of —(CH2)x-NH—CO—, —(CH2)x-NH—CO—(CH2)y, CO—NH—(CH2)x, —$CH_2$—S—$CH_2$—CO— and —S—S—, where x and y are each independently 1-12.

11. The compound of claim 3, wherein said hydrophobic linear amino acid residue is selected from the group consisting of Met and Nle.

12. The compound of claim 3, wherein said linear and branched aliphatic amino acid residue is selected from the group consisting of Leu, Ala, Abu, Nva, Val, Ile, Cys(Me), Met and Nle.

13. The compound of claim 3, wherein said stretch of 0-5 amino acid residues is selected from the group consisting of Phe, Ile, Nle-Tyr-Lys and DLeu-Phe-DLeu-Phe residues.

14. The compound of claim 3, wherein said Xc is selected from the group consisting of Phe residue, N-methyl-Phe residue, 2-oxy-3-phenylpropionic acid derivative and 2-aminoxy-3-phenylpropionic acid derivative.

15. The compound of claim 3, wherein said A-Xa-Xb-Xc-X0 . . . 5- is selected from the group consisting of:
   Formyl-Met-Leu-Phe- (SEQ ID NO: 1)
   Formyl-Met-Leu-Phe-Phe- (SEQ ID NO: 13)
   Formyl-Met-Leu-Phe-Ile- (SEQ ID NO: 14)
   Formyl-Nle-Leu-Phe-Nle-Tyr-Lys- (SEQ ID NO: 15)
   Z-NH-CO-NH-Phe-DLeu-Phe-DLeu-Phe- (SEQ ID NO: 16)
   Formyl-Met-Leu-Phe-Lys- (SEQ ID NO: 17)
   Formyl-Met-Leu-N-methyl-Phe- (SEQ ID NO: 18)
   Formyl-Met-Leu-2-oxy-3-phenylpropionic acid- (SEQ ID NO: 19) and
   Formyl-Met-Leu-2-aminoxy-3-phenylpropionic acid- (SEQ ID NO: 20).

16. A compound having the formula:

$$[Xf\text{-}Xg\text{-}Xh\text{-}Xi\text{-}X0\ldots5]m\text{-}R\text{-}X1\text{-}X2\text{-}X3\text{-}Dab\text{-}X5\text{-}X6\text{-}Dab\text{-}Dab\text{-}X9$$
(with L linker bridging X3 to X9)

wherein
   X1 is a Thr or Ser residue or a covalent bond;
   X2 is selected from the group consisting of Dab and Ser;
   X3 is selected from the group consisting of Lys, Orn, Dap, Glu, Asp, Dab and Cys residues;
   X5 is a hydrophobic amino acid residue;
   X6 is a hydrophobic amino acid residue;
   X9 is selected from the group consisting of Ser, Tyr, Thr, Dab, Lys, Orn, Dap, Glu, Asp, Cys and n-butyric acid residues;
   L is a peptide cyclization linker moiety;
   R is selected from the group consisting of a covalent bond, an amino acid residue, a stretch of amino acid residues, an amino fatty acid residue having 1-12 carbon atoms in its carbon backbone and a polyethylene glycol derivative;
   Xf is selected from the group consisting of Thr, Leu, Gly and Val residues;
   Xg is selected from the group consisting of Lys and Arg residues;
   Xh is selected from the group consisting of Pro, Sar and N-methyl non-polar aliphatic amino acid residues;
   Xi is selected from the group consisting of Arg and Lys residues;
   X0 . . . 5 is 0-5 amino acid residues;
   m is an integer selected from the group consisting of 1-8, whereby if m is greater than 1 [Xf-Xg-Xh-Xi-X0 . . . 5]m is a branched structure;
   with the provisions that said [Xf-Xg-Xh-Xi-X0 . . . 5]m has an immune cell chemotactic activity and that said $$R\text{-}X1\text{-}X2\text{-}X3\text{-}Dab\text{-}X5\text{-}X6\text{-}Dab\text{-}Dab\text{-}X9$$
(with L linker)

has a bacterial outer membrane lipopolysaccharide-binding activity, said immune cell chemotactic activity and said bacterial outer membrane lipopolysaccharide-binding activity acting in synergy to provide a bacterial sensitizing activity.

17. The compound of claim 16, wherein X5 is selected from the group consisting of DPhe, DTrp, DLeu, DNle, DMet, DNva and DVal residues.

18. The compound of claim 16, wherein X5 is selected from the group consisting of Phe, Trp, Leu, Nle, Met, Nva and Val residues.

19. The compound of claim 16, wherein X6 is selected from the group consisting of Leu, Thr, Nva, Val, Met and Ile residues.

20. The compound of claim 16, wherein said stretch of amino acid residues is selected from the group consisting of an oligoAla stretch, an oligoAla stretch interrupted by at least one Glu and/or Asp residue, an oligoGly stretch, and an oligoGly stretch interrupted by at least one Glu and/or Asp residue.

21. The compound of claim 16, wherein said amino fatty acid residue is HN(CH2)xCOOH, where x is 1-12.

22. The compound of claim 16, wherein said amino fatty acid residue is selected from the group consisting of aminocaproic acid residue and aminobutyric acid residue.

23. The compound of claim 16, wherein said cyclization linker moiety is selected from the group consisting of —(CH2)x-NH—CO—, —(CH2)x-NH—CO—(CH2)y, CO—NH—(CH2)x, —CH2—S—CH2—CO—and —S—S—, where x and y are each independently 1-12.

24. The compound of claim 16, wherein [Xf-Xg-Xh-Xi-X0 . . . 5]m- is selected from the group consisting of:

Thr-Lys-Pro-Arg-(SEQ ID NO:21)
   Thr-Arg-Pro-Lys-(SEQ ID NO:22)
   Leu-Lys-Pro-Arg-(SEQ ID NO:23)
   Leu-Arg-Pro-Lys-(SEQ ID NO:24)
   Gly-Lys-Pro-Arg-(SEQ ID NO:25)
   Gly-Arg-Pro-Lys-(SEQ ID NO:26)
   Val-Lys-Pro-Arg-(SEQ ID NO:27)
   Val-Arg-Pro-Lys-(SEQ ID NO:28)
   Thr-Lys-Pro-Arg\
             X—CO—  (SEQ ID NO:29) and
   Thr-Lys-Pro-Arg/

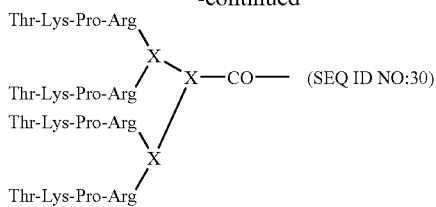 (SEQ ID NO:30)

where X is selected from the group consisting of Dap, Lys and Orn residues.

25. The compound of claim 1, selected from the group consisting of SEQ ID NOs: 3, 4, 6 and 8-11.

26. A pharmaceutical composition for treatment of bacteremia and/or septicemia following infection by gram negative bacteria comprising, as an active ingredient a compound which comprises a bacterial outer membrane lipopolysaccharide-binding peptide conjugated to an immune cell chemotactic peptide, wherein said immune cell chemotactic peptide is selected from the group consisting of formyl chemotactic peptide, desformyl chemotactic peptide, chemotactic peptide with a urea derivative, and tuftsin, said outer membrane lipopolysaccharide-binding peptide and said immune cell chemotactic peptide acting in synergy to provide a bacterial sensitizing activity, wherein said formyl chemotactic peptide comprises an N-terminal N-formyl methionyl residue and said desformyl chemotactic peptide comprises an N-terminal methionyl residue.

27. The pharmaceutical composition of claim 26, wherein said bacterial outer membrane lipopolysaccharide-binding peptide is a polymyxin derivative or a polymyxin analog.

28. A pharmaceutical composition for treatment of bacteremia and/or septicemia following infection by gram negative bacteria comprising, as an active ingredient, a compound having the formula:

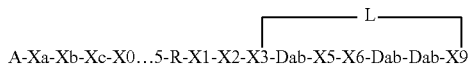

wherein
X1 is a Thr or Ser residue or a covalent bond;
X2 is selected from the group consisting of Dab and Ser;
X3 is selected from the group consisting of Lys, Orn, Dap, Glu, Asp, Dab and Cys residues;
X5 is a hydrophobic amino acid residue;
X6 is a hydrophobic amino acid residue;
X9 is selected from the group consisting of Ser, Tyr, Thr, Dab, Lys, Orn, Dap, Glu, Asp, Cys and n-butyric acid residues;
L is a peptide cyclization linker moiety;
R is selected from the group consisting of a covalent bond, an amino acid residue, a stretch of amino acid residues, an amino fatty acid residue having 1-12 carbon atoms in its carbon backbone and a polyethylene glycol derivative;
Xa is a hydrophobic linear amino acid residue;
Xb is selected from the group consisting of linear and branched aliphatic amino acid residues;
Xc is an aromatic amino acid residue;
A is selected from the group consisting of formyl and Z-NHCONH-, where Z is n-butyl, phenyl, 4-chlorophenyl, 4-methoxyphenyl or p-tolyl derivative;
X0 . . . 5 is a stretch of 0-5 amino acid residues;

with the provisions that said A-Xa-Xb-Xc-X0 . . . 5 has an immune cell chemotactic activity and that said

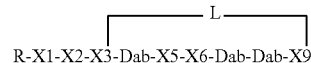

has a bacterial outer membrane lipopolysaccharide-binding activity, said immune cell chemotactic activity and said bacterial outer membrane lipopolysaccharide-binding activity acting in synergy to provide a bacterial sensitizing activity.

29. The pharmaceutical composition of claim 28, wherein X5 is selected from the group consisting of DPhe, DTrp, DLeu, DNle, DMet, DNva and DVal residues.

30. The pharmaceutical composition of claim 28, wherein X5 is selected from the group consisting of Phe, Trp, Leu, Nle, Met, Nva and Val residues.

31. The pharmaceutical composition of claim 28, wherein X6 is selected from the group consisting of Leu, Thr, Nva, Val, Met and Ile residues.

32. The pharmaceutical composition of claim 28, wherein said stretch of amino acid residues is selected from the group consisting of an oligoAla stretch, an oligoAla stretch interrupted by at least one Glu and/or Asp residue, an oligoGly stretch, and an oligoGly stretch interrupted by at least one Glu and/or Asp residue.

33. The pharmaceutical composition of claim 28, wherein said amino fatty acid residue is HN(CH2)xCOOH, where x is 1-12.

34. The pharmaceutical composition of claim 28, wherein said amino fatty acid residue is selected from the group consisting of aminocaproic acid residue and aminobutyric acid residue.

35. The pharmaceutical composition of claim 28, wherein said cyclization linker moiety is selected from the group consisting of —(CH2)x-N—CO—, —(CH2)x-NH—CO—(CH2)y, CO—NH—(CH2)x, —CH$_2$—S—CH$_2$—CO— and —S—S—, where x and y are each independently 1-12.

36. The pharmaceutical composition of claim 28, wherein said hydrophobic linear amino acid residue is selected from the group consisting of Met and Nle.

37. The pharmaceutical composition of claim 28, wherein said linear and branched aliphatic amino acid residue is selected from the group consisting of Leu, Ala, Abu, Nva, Val, Ile, Cys(Me), Met and Nle.

38. The pharmaceutical composition of claim 28, wherein said stretch of 0-5 amino acid residues is selected from the group consisting of Phe, Ile, Nle-Tyr-Lys and DLeu-Phe-DLeu-Phe residues.

39. The pharmaceutical composition of claim 28, wherein said Xc is selected from the group consisting of Phe residue, N-methyl Phe derivative, 2-oxy-3-phenylpropionic acid derivative and 2-aminoxy-3-phenylpropionic acid derivative.

40. The pharmaceutical composition of claim 28, wherein said A-Xa-Xb-Xc-X0 . . . 5- is selected from the group consisting of:
Formyl-Met-Leu-Phe- (SEQ ID NO: 1)
Formyl-Met-Leu-Phe-Phe- (SEQ ID NO: 13)
Formyl-Met-Leu-Phe-Ile- (SEQ ID NO: 14)
Formyl-Nle-Leu-Phe-Nle-Tyr-Lys- (SEQ ID NO: 15)
Z-NH-CO-NH-Phe-DLeu-Phe-DLeu-Phe- (SEQ ID NO: 16)
Formyl-Met-Leu-Phe-Lys- (SEQ ID NO: 17)
Formyl-Met-Leu-N-methyl-Phe- (SEQ ID NO: 18)

Formyl-Met-Leu-2-oxy-3-phenylpropionic acid- (SEQ ID NO: 19) and

Formyl-Met-Leu-2-aminoxy-3-phenylpropionic acid- (SEQ ID NO: 20).

41. A pharmaceutical composition for treatment of bacteremia and/or septicemia following infection by gram negative bacteria comprising, as an active ingredient, a compound having the formula:

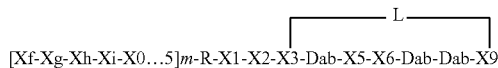

wherein
X1 is a Thr or Ser residue or a covalent bond;
X2 is selected from the group consisting of Dab and Ser;
X3 is selected from the group consisting of Lys, Orn, Dap, Glu, Asp, Dab and Cys residues;
X5 is a hydrophobic amino acid residue;
X6 is a hydrophobic amino acid residue;
X9 is selected from the group consisting of Ser, Tyr, Thr, Dab, Lys, Orn, Dap, Glu, Asp, Cys and n-butyric acid residues;
L is a peptide cyclization linker moiety;
R is selected from the group consisting of a covalent bond, an amino acid residue, a stretch of amino acid residues, an amino fatty acid residue having 1-12 carbon atoms in its carbon backbone and a polyethylene glycol derivative;
Xf is selected from the group consisting of Thr, Leu, Gly and Val residues;
Xg is selected from the group consisting of Lys and Arg residues;
Xh is selected from the group consisting of Pro, Sar and N-methyl non-polar aliphatic amino acid residues;
Xi is selected from the group consisting of Arg and Lys residues;
X0 . . . 5 is 0-5 amino acid residues;
m is an integer selected from the group consisting of 1-8, whereby if m is greater than 1 [Xf-Xg-Xh-Xi-X0 . . . 5]m is a branched structure;
with the provisions that said [Xf-Xg-Xh-Xi-X0 . . . 5]m has an immune cell chemotactic activity and that said

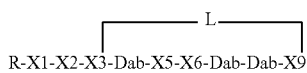

has a bacterial outer membrane lipopolysaccharide-binding activity, said immune cell chemotactic activity and said bacterial outer membrane lipopolysaccharide-binding activity acting in synergy to provide a bacterial sensitizing activity.

42. The pharmaceutical composition of claim 41, wherein X5 is selected from the group consisting of DPhe, DTrp, DLeu, DNle, DMet, DNva and DVal residues.

43. The pharmaceutical composition of claim 41, wherein X5 is selected from the group consisting of Phe, Trp, Leu, Nle, Met, Nva and Val residues.

44. The pharmaceutical composition of claim 41, wherein X6 is selected from the group consisting of Leu, Thr, Nva, Val, Met and Ile residues.

45. The pharmaceutical composition of claim 41, wherein said stretch of amino acid residues is selected from the group consisting of an oligoAla stretch, an oligoAla stretch interrupted by at least one Glu and/or Asp residue, an oligoGly stretch, and an oligoGly stretch interrupted by at least one Glu and/or Asp residue.

46. The pharmaceutical composition of claim 41, wherein said amino fatty acid residue is HN(CH2)xCOOH, where x is 1-12.

47. The pharmaceutical composition of claim 41, wherein said amino fatty acid residue is selected from the group consisting of aminocaproic acid residue and aminobutyric acid residue.

48. The pharmaceutical composition of claim 41, wherein said cyclization linker moiety is selected from the group consisting of —(CH2)x-NH—CO—, —(CH2)x-NH—CO—(CH2)y, CO—NH—(CH2)x, —CH$_2$—S—CH$_2$—CO— and —S S—S—, where x and y are each independently 1-12.

49. The pharmaceutical composition of claim 41, wherein [Xf-Xg-Xh-Xi-X0 . . . 5]m- is selected from the group consisting of:

Thr-Lys-Pro-Arg-(SEQ ID NO:21)
Thr-Arg-Pro-Lys-(SEQ ID NO:22)
Leu-Lys-Pro-Arg-(SEQ ID NO:23)
Leu-Arg-Pro-Lys-(SEQ ID NO:24)
Gly-Lys-Pro-Arg-(SEQ ID NO:25)
Gly-Arg-Pro-Lys-(SEQ ID NO:26)
Val-Lys-Pro-Arg-(SEQ ID NO:27)
Val-Arg-Pro-Lys-(SEQ ID NO:28)

Thr-Lys-Pro-Arg
         \
          X—CO—   (SEQ ID NO:29) and
         /
Thr-Lys-Pro-Arg Thr-Lys-Pro-Arg
              \
               X
              / \
Thr-Lys-Pro-Arg   \
                   X—CO—   (SEQ ID NO:30)
Thr-Lys-Pro-Arg   /
              \ /
               X
              /
Thr-Lys-Pro-Arg where X is selected from the group consisting of Dap, Lys and Orn residues.

50. The composition of claim 26, wherein said compound is selected from the group consisting of SEQ ID NOs: 3, 4, 6 and 8-11.

51. The pharmaceutical composition of claim 26, further comprising an antibiotic compound.

52. The pharmaceutical composition of claim 51, wherein said antibiotic compound is selected from the group consisting of novobiocin, erythromycin, lincomycin, nafcillin, nalidixic acid, rifabutin, rifampin, fusidic acid and vancomycin.

53. The pharmaceutical composition of claim 26, further comprising a pharmaceutically acceptable carrier.

54. A method of treating bacteremia and/or septicemia following infection by gram negative bacteria in a subject, the method comprising:
administering to the subject a therapeutically effective amount of a compound which comprises a bacterial outer cell membrane lipopolysaccharide-binding peptide conjugated to an immune cell chemotactic peptide, wherein said immune cell chemotactic peptide is selected from the group consisting of formyl chemotactic peptide, desformyl chemotactic peptide, chemotactic peptide with a urea derivative, and tuftsin, said outer membrane lipopolysaccharide-binding peptide and said immune cell chemotactic peptide acting in synergy to provide a bacterial sensitizing activity.

55. The method of claim 54, wherein said bacterial outer membrane lipopolysaccharide-binding peptide is a polymyxin derivative or a polymyxin analog.

56. A method of treating bacteremia and/or septicemia following infection by gram negative bacteria in a subject, the method comprising:
administering to the subject a therapeutically effective amount of a compound having the formula:

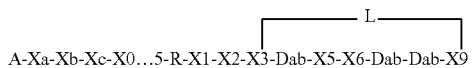
A-Xa-Xb-Xc-X0...5-R-X1-X2-X3-Dab-X5-X6-Dab-Dab-X9 wherein
X1 is a Thr or Ser residue or a covalent bond;
X2 is selected from the group consisting of Dab and Ser;
X3 is selected from the group consisting of Lys, Orn, Dap, Glu, Asp, Dab and Cys residues;
X5 is a hydrophobic amino acid residue;
X6 is a hydrophobic amino acid residue;
X9 is selected from the group consisting of Ser, Tyr, Thr, Dab, Lys, Orn, Dap, Glu, Asp, Cys and n-butyric acid residues;
L is a peptide cyclization linker moiety;
R is selected from the group consisting of a covalent bond, an amino acid residue, a stretch of amino acid residues, an amino fatty acid residue having 1-12 carbon atoms in its carbon backbone and a polyethylene glycol derivative;
Xa is a hydrophobic linear amino acid residue;
Xb is selected from the group consisting of linear and branched aliphatic amino acid residues;
Xc is an aromatic amino acid residue;
A is selected from the group consisting of formyl and Z-NHCONH-, where Z is n-butyl, phenyl, 4-chlorophenyl, 4-methoxyphenyl or p-tolyl derivative;
X0 . . . 5 is a stretch of 0-5 amino acid residues;
with the provisions that said A-Xa-Xb-Xc-X0 . . . 5 has an immune cell chemotactic activity and that said

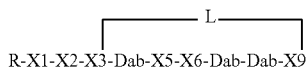
R-X1-X2-X3-Dab-X5-X6-Dab-Dab-X9 has a bacterial outer membrane lipopolysaccharide-binding activity, acid immune cell chemotactic activity and said bacterial outer membrane lipopolysaccharide-binding activity acting in synergy to provide a bacterial sensitizing activity.

57. The method of claim 56, wherein X5 is selected from the group consisting of DPhe, DTrp, DLeu, DNle, DMet, DNva and DVal residues.

58. The method of claim 56, wherein X5 is selected from the group consisting of Phe, Trp, Leu, Nle, Met, Nva and Val residues.

59. The method of claim 56, wherein X6 is selected from the group consisting of Leu, Thr, Nva, Val, Met and Ile residues.

60. The method of claim 56, wherein said stretch of amino acid residues is selected from the group consisting of an oligoAla stretch, an oligoAla stretch interrupted by at least one Glu and/or Asp residue, an oligoGly stretch, and an oligoGly stretch interrupted by at least one Glu and/or Asp residue.

61. The method of claim 56, wherein said amino fatty acid residue is HN(CH2)xCOOH, where x is 1-12.

62. The method of claim 56, wherein said amino fatty acid residue is selected from the group consisting of aminocaproic acid residue and aminobutyric acid residue.

63. The method of claim 56, wherein said cyclization linker moiety is selected from the group consisting of —(CH2)x-NH—CO—, —(CH2)x-NH—CO—(CH2)y, CO—NH—(CH2)x, —CH$_2$—S—CH$_2$—CO— and —S—S—, where x and y are each independently 1-12.

64. The method of claim 56, wherein said hydrophobic linear amino acid residue is selected from the group consisting of Met and Nle.

65. The method of claim 56, wherein said linear and branched aliphatic amino acid residue is selected from the group consisting of Leu, Ala, Abu, Nva, Val, Ile, Cys(Me), Met and Nle.

66. The method of claim 56, wherein said stretch of 0-5 amino acid residues is selected from the group consisting of Phe, Ile, Nle-Tyr-Lys and DLeu-Phe-DLeu-Phe residues.

67. The method of claim 56, wherein said Xc is selected from the group consisting of Phe residue, N-methyl Phe derivative, 2-oxy-3-phenylpropionic acid derivative and 2-aminoxy-3-phenylpropionic acid derivative.

68. The method of claim 56, wherein said A-Xa-Xb-Xc-X0 . . . 5- is selected from the group consisting of:
Formyl-Met-Leu-Phe- (SEQ ID NO: 1)
Formyl-Met-Leu-Phe-Phe- (SEQ ID NO: 13)
Formyl-Met-Leu-Phe-Ile- (SEQ ID NO: 14)
Formyl-Nle-Leu-Phe-Nle-Tyr-Lys- (SEQ ID NO: 15)
Z-NH-CO-NH-Phe-DLeu-Phe-DLeu-Phe- (SEQ ID NO: 16)
Formyl-Met-Leu-Phe-Lys- (SEQ ID NO: 17)
Formyl-Met-Leu-N-methyl-Phe- (SEQ ID NO: 18)
Formyl-Met-Leu-2-oxy-3-phenylpropionic acid- (SEQ ID NO: 19) and
Formyl-Met-Leu-2-aminoxy-3-phenylpropionic acid- (SEQ ID NO: 20).

69. A method of treating bacteremia and/or septicemia following infection by gram negative bacteria in a subject, the method comprising:
administering to the subject a therapeutically effective amount of a compound having the formula:

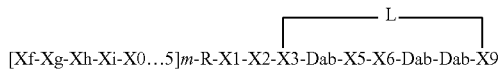
[Xf-Xg-Xh-Xi-X0...5]m-R-X1-X2-X3-Dab-X5-X6-Dab-Dab-X9 wherein
X1 is a Thr or Ser residue or a covalent bond;
X2 is selected from the group consisting of Dab and Ser;
X3 is selected from the group consisting of Lys, Orn, Dap, Glu, Asp, Dab and Cys residues;
X5 is a hydrophobic amino acid residue;
X6 is a hydrophobic amino acid residue;
X9 is selected from the group consisting of Ser, Tyr, Thr, Dab, Lys, Orn, Dap, Glu, Asp, Cys and n-butyric acid residues;
L is a peptide cyclization linker moiety;
R is selected from the group consisting of a covalent bond, an amino acid residue, a stretch of amino acid residues, an amino fatty acid residue having 1-12 carbon atoms in its carbon backbone and a polyethylene glycol derivative;
Xf is selected from the group consisting of Thr, Leu, Gly and Val residues;

Xg is selected from the group consisting of Lys and Arg residues;

Xh is selected from the group consisting of Pro, Sar and N-methyl non-polar aliphatic amino acid residues;

Xi is selected from the group consisting of Arg and Lys residues;

X0 . . . 5 is 0-5 amino acid residues;

m is an integer selected from the group consisting of 1-8, whereby if m is greater than 1 [Xf-Xg-Xh-Xi-X0 . . . 5]m is a branched structure;

with the provisions that said [Xf-Xg-Xh-Xi-X0 . . . 5]m has an immune cell chemotactic activity and that said

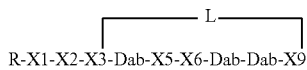

has a bacterial outer membrane lipopolysaccharide-binding activity, said immune cell chemotactic activity and said bacterial outer membrane lipopolysaccharide-binding activity acting in synergy to provide a bacterial sensitizing activity.

70. The method of claim 69, wherein X5 is selected from the group consisting of DPhe, DTrp, DLeu, DNle, DMet, DNva and DVal residues.

71. The method of claim 69, wherein X5 is selected from the group consisting of Phe, Trp, Leu, Nle, Met, Nva and Val residues.

72. The method of claim 69, wherein X6 is selected from the group consisting of Leu, Thr, Nva, Val, Met and Ile residues.

73. The method of claim 69, wherein said stretch of amino acid residues is selected from the group consisting of an oligoAla stretch, an oligoAla stretch interrupted by at least one Glu and/or Asp residue, an oligoGly stretch, and an oligoGly stretch interrupted by at least one Glu and/or Asp residue.

74. The method of claim 69, wherein said amino fatty acid residue is HN(CH2)xCOOH, where x is 1-12.

75. The method of claim 69, wherein said amino fatty acid residue is selected from the group consisting of aminocaproic acid residue and aminobutyric acid residue.

76. The method of claim 69, wherein said cyclization linker moiety is selected from the group consisting of —(CH2)x-NH—CO—, —(CH2)x-NH—CO—(CH2)y, CO—NH—(CH2)x, —CH$_2$—S—CH$_2$—CO— and —S—S—, where x and y are each independently 1-12.

77. The method of claim 69, wherein [Xf-Xg-Xh-Xi-X0 . . . 5]m- is selected from the group consisting of:

Thr-Lys-Pro-Arg-(SEQ ID NO:21)
Thr-Arg-Pro-Lys-(SEQ ID NO:22)
Leu-Lys-Pro-Arg-(SEQ ID NO:23)
Leu-Arg-Pro-Lys-(SEQ ID NO:24)
Gly-Lys-Pro-Arg-(SEQ ID NO:25)
Gly-Arg-Pro-Lys-(SEQ ID NO:26)
Val-Lys-Pro-Arg-(SEQ ID NO:27)
Val-Arg-Pro-Lys-(SEQ ID NO:28)

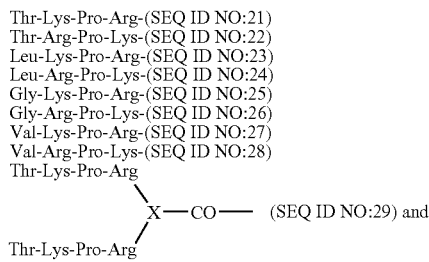

-continued

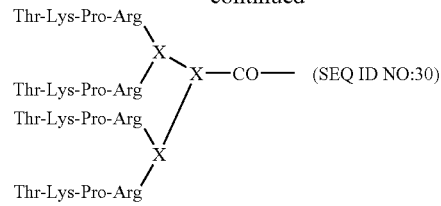

where X is selected from the group consisting of Dap, Lys and Orn residues.

78. The method of claim 54, wherein the compound is selected from the group consisting of SEQ ID NOs: 3, 4, 6 and 8-11.

79. The method of claim 54, further comprising administering an antibiotic compound.

80. The method of claim 79, wherein said antibiotic compound is selected from the group consisting of novobiocin, erythromycin, lincomycin, nafcillin, naladixic acid, rifabutin, rifampin, fusidic acid and vancomycin.

81. The compound of claim 4, wherein X5 is selected from the group consisting of DPhe and DLeu.

82. The compound of claim 81, wherein X6 is selected from the group consisting of Leu, Thr, Nva, Val, Met and Ile residues.

83. The compound of claim 82, wherein said cyclization linker moiety is selected from the group consisting of —(CH2)x-NH—CO—, —(CH2)x-NH—CO—(CH2)y, CO—NH—(CH2)x, —CH$_2$—S—CH$_2$—CO— and —S—S—, where x and y are each independently 1-12.

84. The compound of claim 82, wherein said A-Xa-Xb-Xc-X0 . . . 5- is selected from the group consisting of:
Formyl-Met-Leu-Phe- (SEQ ID NO: 1)
Formyl-Met-Leu-Phe-Phe- (SEQ ID NO: 13)
Formyl-Met-Leu-Phe-Ile- (SEQ ID NO: 14)
Formyl-Nle-Leu-Phe-Nle-Tyr-Lys- (SEQ ID NO: 15)
Z-NH-CO-NH-Phe-DLeu-Phe-DLeu-Phe- (SEQ ID NO: 16)
Formyl-Met-Leu-Phe-Lys- (SEQ ID NO: 17)
Formyl-Met-Leu-N-methyl-Phe- (SEQ ID NO: 18)
Formyl-Met-Leu-2-oxy-3-phenylpropionic acid- (SEQ ID NO: 19) and
Formyl-Met-Leu-2-aminoxy-3-phenylpropionic acid- (SEQ ID NO: 20).

85. The pharmaceutical composition of claim 28, wherein X5 is selected from the group consisting of DPhe and DLeu.

86. The pharmaceutical composition of claim 85, wherein X6 is selected from the group consisting of Leu, Thr, Nva, Val, Met and Ile residues.

87. The pharmaceutical composition of claim 86, wherein said cyclization linker moiety is selected from the group consisting of —(CH2)x-NH—CO—, —(CH2)x-NH—CO—(CH2)y, CO—NH—(CH2)x, —CH$_2$—S—CH$_2$—CO— and —S—S—, where x and y are each independently 1-12.

88. The pharmaceutical composition of claim 86, wherein said A-Xa-Xb-Xc-X0 . . . 5- is selected from the group consisting of:
Formyl-Met-Leu-Phe- (SEQ ID NO: 1)
Formyl-Met-Leu-Phe-Phe- (SEQ ID NO: 13)
Formyl-Met-Leu-Phe-Ile- (SEQ ID NO: 14)
Formyl-Nle-Leu-Phe-Nle-Tyr-Lys- (SEQ ID NO: 15)
Z-NH-CO-NH-Phe-DLeu-Phe-DLeu-Phe- (SEQ ID NO: 16)
Formyl-Met-Leu-Phe-Lys- (SEQ ID NO: 17)

Formyl-Met-Leu-N-methyl-Phe- (SEQ ID NO: 18)
Formyl-Met-Leu-2-oxy-3-phenylpropionic acid- (SEQ ID NO: 19) and
Formyl-Met-Leu-2-aminoxy-3-phenylpropionic acid- (SEQ ID NO: 20).

89. The method of claim 56, wherein X5 is selected from the group consisting of DPhe and DLeu.

90. The method of claim 89, wherein X6 is selected from the group consisting of Leu, Thr, Nva, Val, Met and Ile residues.

91. The method of claim 90, wherein said cyclization linker moiety is selected from the group consisting of —(CH2)x-NH—CO—, —(CH2)x-NH—CO—(CH2)y, CO—NH—(CH2)x, —CH$_2$—S—CH$_2$—CO— and —S—S—, where x and y are each independently 1-12.

92. The method of claim 90, wherein said A-Xa-Xb-Xc-X0 . . . 5- is selected from the group consisting of:
Formyl-Met-Leu-Phe- (SEQ ID NO: 1)
Formyl-Met-Leu-Phe-Phe- (SEQ ID NO: 13)
Formyl-Met-Leu-Phe-Ile- (SEQ ID NO: 14)
Formyl-Nle-Leu-Phe-Nle-Tyr-Lys- (SEQ ID NO: 15)
Z-NH-CO-NH-Phe-DLeu-Phe-DLeu-Phe- (SEQ ID NO: 16)
Formyl-Met-Leu-Phe-Lys- (SEQ ID NO: 17)
Formyl-Met-Leu-N-methyl-Phe- (SEQ ID NO: 18)
Formyl-Met-Leu-2-oxy-3-phenylpropionic acid- (SEQ ID NO: 19) and
Formyl-Met-Leu-2-aminoxy-3-phenylpropionic acid- (SEQ ID NO: 20).

93. The pharmaceutical composition of claim 28, further comprising an antibiotic compound.

94. The pharmaceutical composition of claim 93, wherein said antibiotic compound is selected from the group consisting of novobiocin, erythromycin, lincomycin, nafcillin, naladixic acid, rifabutin, rifampin, fusidic acid and vancomycin.

95. The pharmaceutical composition of claim 28, further comprising a pharmaceutically acceptable carrier.

96. The pharmaceutical composition of claim 41, further comprising an antibiotic compound.

97. The pharmaceutical composition of claim 96, wherein said antibiotic compound is selected from the group consisting of novobiocin, erythromycin, lincomycin, nafcillin, naladixic acid, rifabutin, rifampin, fusidic acid and vancomycin.

98. The pharmaceutical composition of claim 41, further comprising a pharmaceutically acceptable carrier.

99. The method of claim 56, further comprising administering an antibiotic compound.

100. The method of claim 99, wherein said antibiotic compound is selected from the group consisting of novobiocin, erythromycin, lincomycin, nafcillin, naladixic acid, rifabutin, rifampin, fusidic acid and vancomycin.

101. The method of claim 69, further comprising administering an antibiotic compound.

102. The method of claim 101, wherein said antibiotic compound is selected from the group consisting of novobiocin, erythromycin, lincomycin, nafcillin, naladixic acid, rifabutin, rifampin, fusidic acid and vancomycin.

* * * * *

SEQUENCE LISTING

```
<160> NUMBER OF SEQ ID NOS: 12

<210> SEQ ID NO 1
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-formyl-methionyl

<400> SEQUENCE: 1

Xaa Leu Phe
1

<210> SEQ ID NO 2
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Di-amino butyric acid (Dab)
<220> FEATURE:
<221> NAME/KEY: misc_feature
```

```
<222> LOCATION: (5)..(5)
<223> OTHER INFORMATION: D-Phenylalanine
<220> FEATURE:
<221> NAME/KEY: misc_feature
<222> LOCATION: (7)..(8)
<223> OTHER INFORMATION: Di-amino butyric acid (Dab)
<220> FEATURE:
<221> NAME/KEY: misc_feature
<222> LOCATION: (3)..(9)
<223> OTHER INFORMATION: Cyclic peptide

<400> SEQUENCE: 2

Thr Xaa Xaa Xaa Xaa Leu Xaa Xaa Thr
1               5

<210> SEQ ID NO 3
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-formyl-methionyl
<220> FEATURE:
<221> NAME/KEY: misc_feature
<222> LOCATION: (5)..(7)
<223> OTHER INFORMATION: Di-amino butyric acid (Dab)
<220> FEATURE:
<221> NAME/KEY: misc_feature
<222> LOCATION: (8)..(8)
<223> OTHER INFORMATION: D-phenylalanine
<220> FEATURE:
<221> NAME/KEY: misc_feature
<222> LOCATION: (10)..(11)
<223> OTHER INFORMATION: Di-amino butyric acid (Dab)
<220> FEATURE:
<221> NAME/KEY: misc_feature
<222> LOCATION: (6)..(12)
<223> OTHER INFORMATION: Cyclic peptide

<400> SEQUENCE: 3

Xaa Leu Phe Thr Xaa Xaa Xaa Xaa Leu Xaa Xaa Thr
1               5                   10

<210> SEQ ID NO 4
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (6)..(8)
<223> OTHER INFORMATION: Di-amino butyric acid (Dab)
<220> FEATURE:
<221> NAME/KEY: misc_feature
<222> LOCATION: (9)..(9)
<223> OTHER INFORMATION: D-phenylalanine
<220> FEATURE:
<221> NAME/KEY: misc_feature
<222> LOCATION: (11)..(12)
<223> OTHER INFORMATION: Di-amino butyric acid (Dab)
<220> FEATURE:
<221> NAME/KEY: misc_feature
<222> LOCATION: (7)..(13)
<223> OTHER INFORMATION: Cyclic peptide

<400> SEQUENCE: 4

Thr Leu Pro Arg Thr Xaa Xaa Xaa Xaa Leu Xaa Xaa Thr
1               5                   10
```

```
<210> SEQ ID NO 5
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Di-amino butyric acid (Dab)
<220> FEATURE:
<221> NAME/KEY: misc_feature
<222> LOCATION: (4)..(4)
<223> OTHER INFORMATION: D-phenylalanine
<220> FEATURE:
<221> NAME/KEY: misc_feature
<222> LOCATION: (6)..(7)
<223> OTHER INFORMATION: Di-amino butyric acid (Dab)
<220> FEATURE:
<221> NAME/KEY: misc_feature
<222> LOCATION: (2)..(8)
<223> OTHER INFORMATION: Cyclic peptide

<400> SEQUENCE: 5

Xaa Xaa Xaa Xaa Leu Xaa Xaa Thr
 1               5

<210> SEQ ID NO 6
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-formyl-methionyl
<220> FEATURE:
<221> NAME/KEY: misc_feature
<222> LOCATION: (4)..(6)
<223> OTHER INFORMATION: Di-amino butyric acid (Dab)
<220> FEATURE:
<221> NAME/KEY: misc_feature
<222> LOCATION: (7)..(7)
<223> OTHER INFORMATION: D-Phenylalanine
<220> FEATURE:
<221> NAME/KEY: misc_feature
<222> LOCATION: (9)..(10)
<223> OTHER INFORMATION: Di-amino butyric acid (Dab)
<220> FEATURE:
<221> NAME/KEY: misc_feature
<222> LOCATION: (5)..(11)
<223> OTHER INFORMATION: Cyclic peptide

<400> SEQUENCE: 6

Xaa Leu Phe Xaa Xaa Xaa Xaa Leu Xaa Xaa Thr
 1               5                  10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: H-Lysin
<220> FEATURE:
<221> NAME/KEY: misc_feature
<222> LOCATION: (4)..(10)
<223> OTHER INFORMATION: Cyclic Hydroxy-peptide

<400> SEQUENCE: 7
```

```
Xaa Thr Lys Cys Lys Phe Leu Lys Lys Cys
1               5                   10
```

<210> SEQ ID NO 8
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: H-Threonine
<220> FEATURE:
<221> NAME/KEY: misc_feature
<222> LOCATION: (1)..(1)
<223> OTHER INFORMATION: H-Threonine
<220> FEATURE:
<221> NAME/KEY: misc_feature
<222> LOCATION: (1)..(1)
<223> OTHER INFORMATION: H-Threonine
<220> FEATURE:
<221> NAME/KEY: misc_feature
<222> LOCATION: (8)..(14)
<223> OTHER INFORMATION: Cyclic Hydroxy-peptide

<400> SEQUENCE: 8

```
Xaa Lys Pro Arg Lys Thr Lys Cys Lys Phe Leu Lys Lys Cys
1               5                   10
```

<210> SEQ ID NO 9
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: H-Threonine
<220> FEATURE:
<221> NAME/KEY: misc_feature
<222> LOCATION: (11)..(17)
<223> OTHER INFORMATION: Cyclic Hydroxy-peptide

<400> SEQUENCE: 9

```
Xaa Lys Pro Arg Ala Ala Ala Lys Thr Lys Cys Lys Phe Leu Lys Lys
1               5                   10                  15

Cys
```

<210> SEQ ID NO 10
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-formyl-methionyl
<220> FEATURE:
<221> NAME/KEY: misc_feature
<222> LOCATION: (7)..(13)
<223> OTHER INFORMATION: Cyclic Hydroxy-peptide

<400> SEQUENCE: 10

```
Xaa Leu Phe Lys Thr Lys Cys Lys Phe Leu Lys Lys Cys
1               5                   10
```

<210> SEQ ID NO 11
<211> LENGTH: 17

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-formyl-methionyl
<220> FEATURE:
<221> NAME/KEY: misc_feature
<222> LOCATION: (10)..(16)
<223> OTHER INFORMATION: Cyclic Hydroxy-peptide

<400> SEQUENCE: 11

Xaa Leu Phe Ala Ala Ala Lys Thr Lys Cys Lys Lys Phe Leu Lys Lys
1               5                   10                  15

Cys

<210> SEQ ID NO 12
<211> LENGTH: 4
<212> TYPE: PRT
<213> ORGANISM: Artificial sequence
<220> FEATURE:
<223> OTHER INFORMATION: Synthetic peptide

<400> SEQUENCE: 12

Thr Lys Pro Arg
```